(12) United States Patent
Röbling et al.

(10) Patent No.: US 10,835,298 B2
(45) Date of Patent: *Nov. 17, 2020

(54) PROCESS FOR INTRODUCING A STABILIZING ELEMENT INTO A VERTEBRAL ELEMENT

(71) Applicant: Evospine GmbH, Eltville am Rhein (DE)

(72) Inventors: Christian Röbling, Freiburg (DE); Claudia Rieger, Halle/Saale (DE); Farman Hedayat, Cologne (DE)

(73) Assignee: Evospine GmbH, Eltville am Rhein (DE)

( * ) Notice: Subject to any disclaimer, the term of this patent is extended or adjusted under 35 U.S.C. 154(b) by 174 days.

This patent is subject to a terminal disclaimer.

(21) Appl. No.: 14/857,149

(22) Filed: Sep. 17, 2015

(65) Prior Publication Data

US 2016/0081724 A1 Mar. 24, 2016

Related U.S. Application Data

(62) Division of application No. 12/912,115, filed on Oct. 26, 2010, now Pat. No. 9,220,535.

(51) Int. Cl.
*A61B 17/70* (2006.01)
*A61F 2/44* (2006.01)
(Continued)

(52) U.S. Cl.
CPC ...... *A61B 17/7082* (2013.01); *A61B 17/7001* (2013.01); *A61B 17/844* (2013.01); *A61B 17/8625* (2013.01); *A61B 17/8685* (2013.01); *A61F 2/4425* (2013.01); *A61F 2/4455* (2013.01); *A61F 2/4611* (2013.01); (Continued)

(58) Field of Classification Search
CPC .. A61F 2002/30131; A61F 2002/30471; A61F 2002/20505; A61F 2/4611; A61F 2/4455–447; A61B 17/844; A61B 17/8685; A61B 2017/681; A61B 17/7032
See application file for complete search history.

(56) References Cited

U.S. PATENT DOCUMENTS 6,056,749 A * 5/2000 Kuslich ............... A61B 17/025
606/247
6,368,351 B1 4/2002 Glenn et al.
(Continued)

FOREIGN PATENT DOCUMENTS

EP 0 965 313 12/1999
FR 2 771 282 5/1999
(Continued)

OTHER PUBLICATIONS

Recoules-Arche et al. "Extra-Foraminal Lumbar Interbody Fusion (ELIF) 30 Degenerative Lumbar Dislocations. 1 Year Follow-Up", RACHIS. vol. 16, No. 3, Sep. 2004 (Year: 2004).*
(Continued)

*Primary Examiner* — Ellen C Hammond
(74) *Attorney, Agent, or Firm* — Smartpat PLC

(57) ABSTRACT

A process for introducing a stabilizing element into a vertebral column, in which the stabilizing element is introduced in such a manner that the stabilizing element connects two adjacent vertebral bodies to one another.

8 Claims, 38 Drawing Sheets

(51) Int. Cl.
*A61F 2/46* (2006.01)
*A61B 17/84* (2006.01)
*A61B 17/86* (2006.01)
*A61B 17/68* (2006.01)
*A61F 2/30* (2006.01)

(52) U.S. Cl.
CPC . *A61B 2017/681* (2013.01); *A61F 2002/3008* (2013.01); *A61F 2002/30092* (2013.01); *A61F 2002/30131* (2013.01); *A61F 2002/30133* (2013.01); *A61F 2002/30143* (2013.01); *A61F 2002/30166* (2013.01); *A61F 2002/30176* (2013.01); *A61F 2002/30179* (2013.01); *A61F 2002/30471* (2013.01); *A61F 2002/30484* (2013.01); *A61F 2002/30505* (2013.01); *A61F 2002/30507* (2013.01); *A61F 2002/30523* (2013.01); *A61F 2002/30565* (2013.01); *A61F 2002/30566* (2013.01); *A61F 2002/30571* (2013.01); *A61F 2002/30579* (2013.01); *A61F 2002/30594* (2013.01); *A61F 2002/30624* (2013.01); *A61F 2002/30632* (2013.01); *A61F 2002/30975* (2013.01); *A61F 2002/4627* (2013.01); *A61F 2002/4628* (2013.01)

(56) References Cited

U.S. PATENT DOCUMENTS

| | | | |
|---|---|---|---|
| 6,432,140 B1* | 8/2002 | Lin | A61B 17/70 606/247 |
| 6,454,807 B1 | 9/2002 | Jackson | |
| 6,485,518 B1* | 11/2002 | Cornwall | A61B 17/7064 128/898 |
| 6,558,386 B1* | 5/2003 | Cragg | A61B 17/1642 606/279 |
| 7,682,394 B2* | 3/2010 | Recoules-Arche | A61F 2/4455 623/17.11 |
| 7,740,635 B2* | 6/2010 | Lieberman | A61B 17/1757 606/104 |
| 9,220,535 B2* | 12/2015 | Robling | A61B 17/7001 |
| 9,492,201 B2* | 11/2016 | Reiley | A61B 17/1615 |
| 9,561,063 B2* | 2/2017 | Reiley | A61B 17/1615 |
| 2002/0016583 A1* | 2/2002 | Cragg | A61B 17/1671 604/500 |
| 2002/0198527 A1 | 12/2002 | Muckter | |
| 2003/0181982 A1* | 9/2003 | Kuslich | A61B 17/7055 623/17.16 |
| 2004/0073216 A1* | 4/2004 | Lieberman | A61B 17/1604 606/279 |
| 2004/0249461 A1 | 12/2004 | Ferree | |
| 2005/0021114 A1 | 1/2005 | Hidaka | |
| 2005/0075644 A1* | 4/2005 | DiPoto et al. | A61B 1/313 |
| 2005/0143735 A1 | 6/2005 | Kyle | |
| 2005/0154461 A1* | 7/2005 | Humphreys | A61F 2/4405 623/17.11 |
| 2005/0261695 A1* | 11/2005 | Cragg | A61B 17/1671 606/86 R |
| 2006/0004326 A1* | 1/2006 | Collins et al. | A61F 2/44 |
| 2006/0004448 A1 | 1/2006 | Casey | |
| 2006/0052788 A1 | 3/2006 | Thelen et al. | |
| 2006/0217806 A1* | 9/2006 | Peterman | A61F 2/4455 623/17.11 |
| 2006/0235388 A1* | 10/2006 | Justis | A61B 17/70 606/263 |
| 2006/0287725 A1* | 12/2006 | Miller | A61F 2/4455 623/17.11 |
| 2007/0016298 A1* | 1/2007 | Recoules-Arche | A61F 2/4455 623/17.11 |
| 2007/0106383 A1* | 5/2007 | Abdou | A61B 17/70 623/17.11 |
| 2007/0233260 A1* | 10/2007 | Cragg | A61B 17/1671 623/17.12 |
| 2008/0033432 A1* | 2/2008 | McGraw | A61B 17/70 606/86 A |
| 2008/0103597 A1* | 5/2008 | Lechmann | A61F 2/4425 623/17.16 |
| 2008/0119932 A1* | 5/2008 | Lechmann | A61F 2/4425 623/17.11 |
| 2008/0132901 A1* | 6/2008 | Recoules-Arche | A61F 2/4465 606/99 |
| 2008/0133015 A1* | 6/2008 | Lechmann | A61F 2/446 623/17.16 |
| 2008/0154377 A1 | 6/2008 | Voellmicke | |
| 2008/0172060 A1* | 7/2008 | Collins | A61B 17/8811 606/94 |
| 2008/0221623 A1 | 9/2008 | Gooch | |
| 2008/0300601 A1* | 12/2008 | Fabian | A61B 17/025 606/90 |
| 2009/0048676 A1 | 2/2009 | Fabian | |
| 2009/0112269 A1* | 4/2009 | Lieberman | A61B 17/7064 606/301 |
| 2009/0131992 A1 | 5/2009 | Greenhalgh et al. | |
| 2009/0157186 A1* | 6/2009 | Magerl | A61F 2/4455 623/17.16 |
| 2009/0270873 A1* | 10/2009 | Fabian | A61F 2/442 606/99 |
| 2010/0016973 A1 | 1/2010 | De Villiers et al. | |
| 2010/0168751 A1 | 7/2010 | Anderson et al. | |
| 2011/0009907 A1* | 1/2011 | Klein | A61B 17/1642 606/279 |
| 2011/0054538 A1* | 3/2011 | Zehavi | A61F 2/4455 606/279 |
| 2011/0118790 A1* | 5/2011 | Reiley | A61B 17/1615 606/279 |
| 2011/0125268 A1* | 5/2011 | Reiley | A61B 17/1615 623/17.11 |
| 2012/0271424 A1* | 10/2012 | Crawford | A61B 17/1631 623/17.16 |

FOREIGN PATENT DOCUMENTS

| | | |
|---|---|---|
| WO | WO 00/40179 | 7/2000 |
| WO | WO 2004/037067 | 5/2004 |
| WO | WO 00/25706 | 2/2009 |
| WO | WO 2010/092613 | 8/2010 |

OTHER PUBLICATIONS

Kurzbuch et al. "Minimal invasive lumbar spine revision surgery at distance from the dura and postsurgical scar tissue: extraforaminal Lumbar Interbody Fusion (ELIF)", Journal of Clinical Neuroscience. 47(2018) 332-336 (Year: 2017).*

EPC Search Report, No. 10 013 960.9 dated Mar. 28, 2011, 8 pgs,—German; 5 pgs.—English.

EPC Search Report No. 10 013 959.1 dated Apr. 11, 2011 9 pgs.—German; 4 pgs.—English.

* cited by examiner

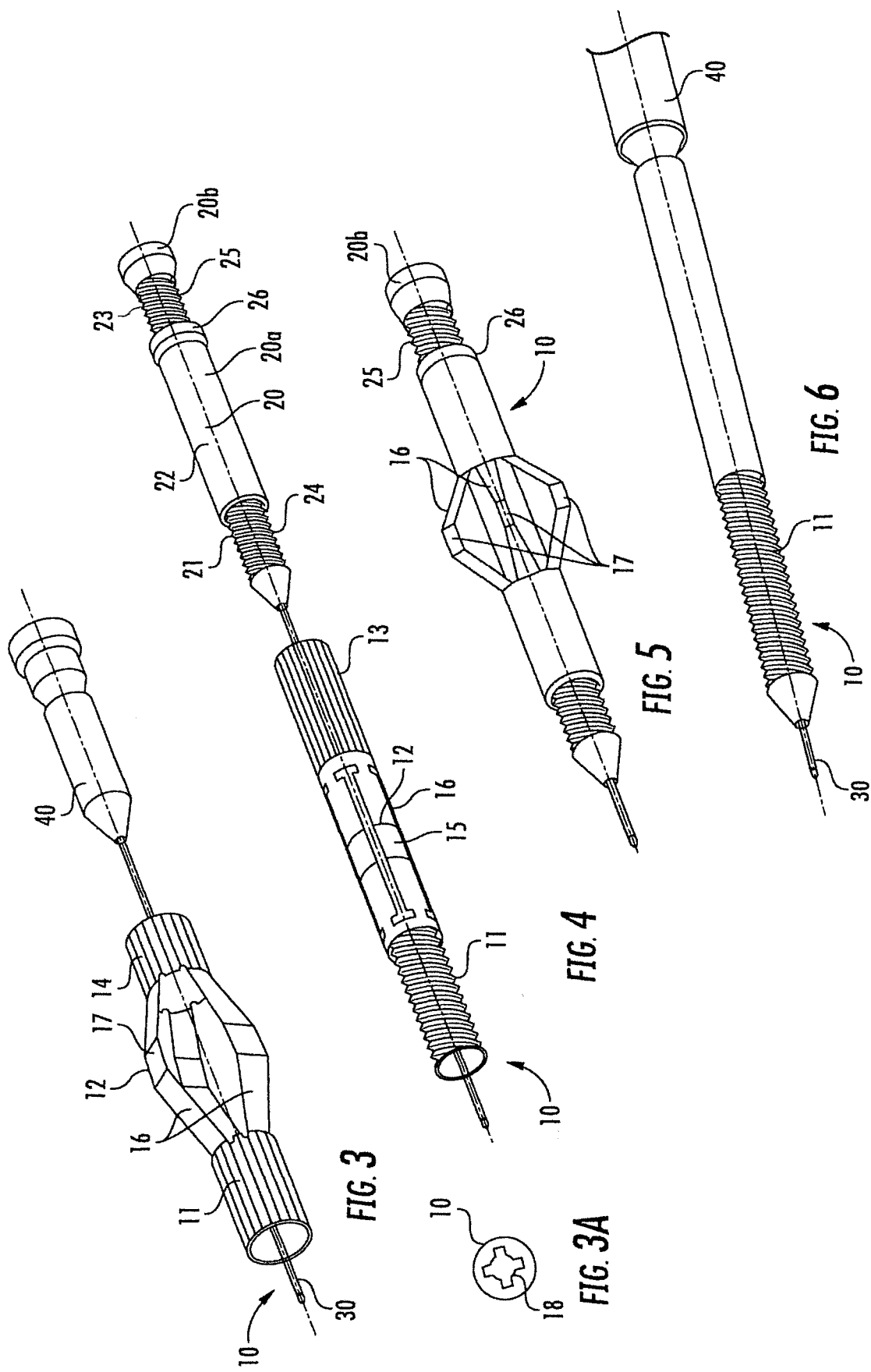

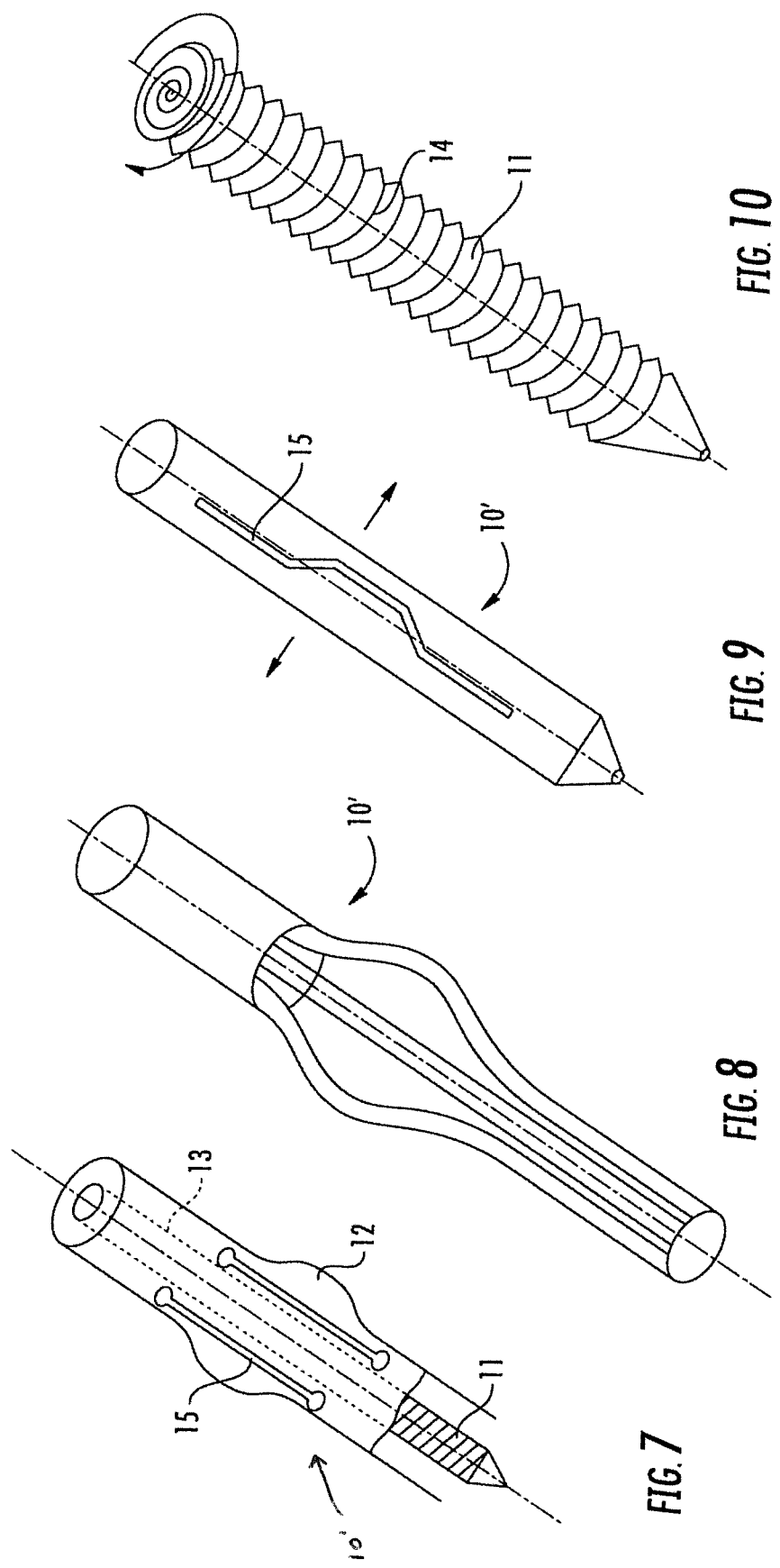

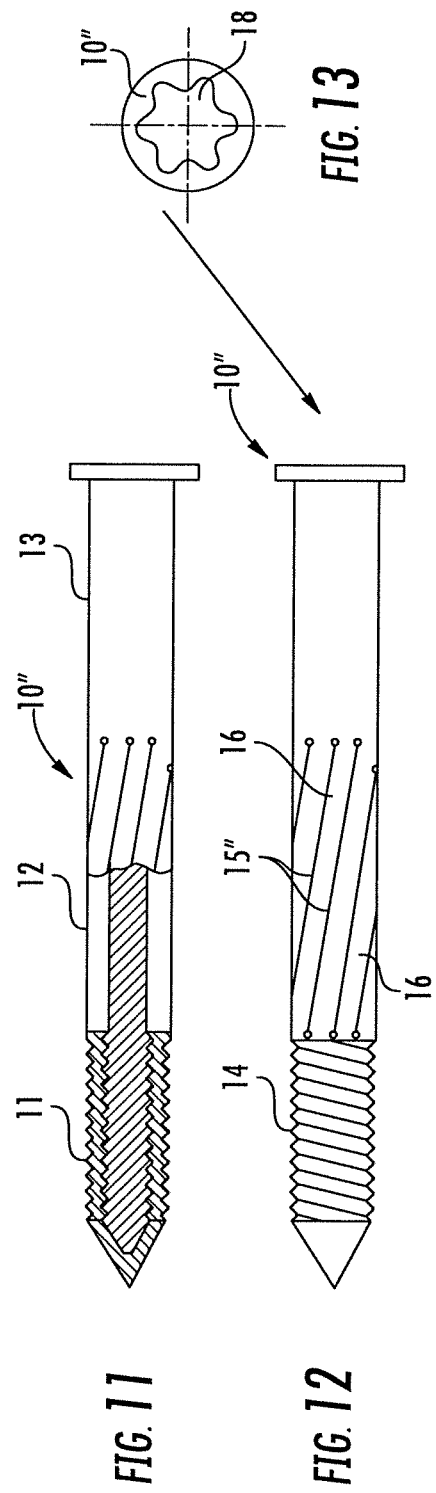
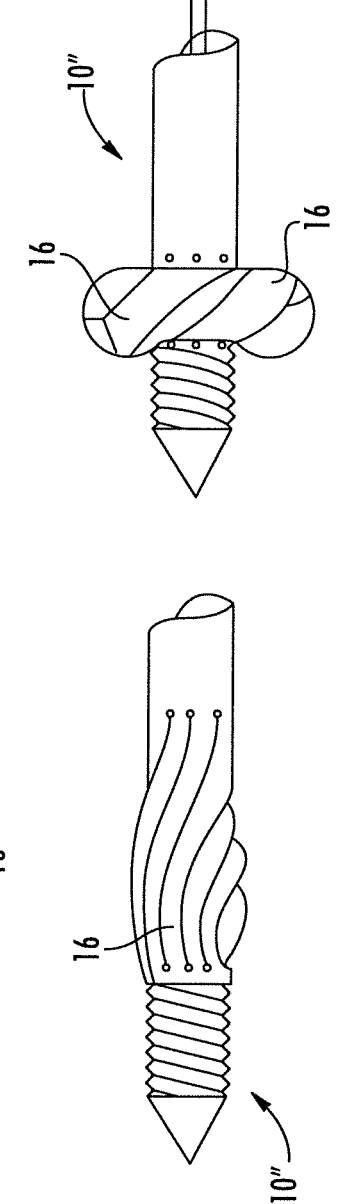
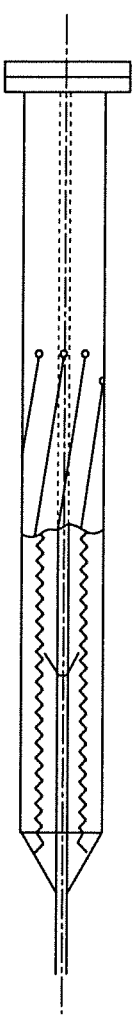
FIG. 11
FIG. 12
FIG. 13
FIG. 14
FIG. 15
FIG. 16
FIG. 17

PROCESS FOR INTRODUCING A STABILIZING ELEMENT INTO A VERTEBRAL ELEMENT

CROSS REFERENCE TO RELATED APPLICATIONS

This application relates to and is a divisional of U.S. Ser. No. 12/912,115 filed Oct. 26, 2010, the entire contents of which are incorporated herein by reference.

FIGURE FOR PUBLICATION

FIG. 1

BACKGROUND OF THE INVENTION

1. Field of the Invention

The present invention relates to a process for introducing a stabilizing element into a vertebral column as well as the process for introducing an intervertebral disk prosthesis into an intervertebral space.

2. Description of the Related Art

It is known that a vertebral column can be stabilized in that adjacent vertebral bodies are connected to each other by a rod system. To this end, several, in particular four, pedicle screws are inserted transversely to the longitudinal axis of the vertebral column into the adjacent vertebral bodies and each two pedicle screws of adjacent vertebral bodies are connected to one another by a rod. Such a stabilization requires a considerable intervention in the patient and entails as a rule a soft-tissue trauma over a length of 10 cm or more.

It is furthermore known that an intervertebral disk prosthesis can be introduced between two adjacent vertebral bodies in order to replace a defective intervertebral disk. In order to insert such a intervertebral disk prosthesis, various operation procedures were developed. The best-known processes are the ventrally performed vertebral body fusion, called ALIF (anterior lumbar interbody fusion), the dorsally performed vertebral body fusion, called PLIF (posterior lumbar interbody fusion) and the transforaminal vertebral body fusion, performed via a dorsolateral access, called TLIF (transforaminal lumbar interbody fusion) (cf. FIG. 49). These interventions also require a considerable intervention in the patient.

The invention solves the problem by making available a process for the stabilizing of a vertebral column that brings about a reliable stabilization of the vertebral column with few components and that in particular causes only a slight trauma to the soft tissue.

The invention solves the problem with a process for the introduction of a stabilizing element into a vertebral column as well as with a process for introducing an intervertebral disk prosthesis into an intervertebral space between two adjacent vertebral bodies.

ASPECTS AND SUMMARY OF THE INVENTION

The process in accordance with the invention for introducing a stabilizing element into a vertebral column is distinguished in that the stabilizing element is introduced in such a manner that the stabilizing element connects two adjacent vertebral bodies to one another. The connection takes place, in particular, directly via the stabilizing element. Thus, there is the possibility of stabilizing a vertebral column, in particular two adjacent vertebral bodies with a single stabilizing element.

According to a preferred embodiment of the invention, the stabilizing element passes through each of the two adjacent vertebral bodies in the longitudinal direction of the vertebral column at least in sections. As a result, a direct connection of the two adjacent vertebral bodies is directly achieved by the stabilizing element itself. Thus, a plurality of components to be introduced, such as is necessary in a rod system, is eliminated.

The stabilizing element is introduced in an especially advantageous manner through a single access point so that the intervention can take place in particular in a minimally invasive manner and severe trauma to the soft tissue can be avoided in the patient. The access point is preferably dorsomedially arranged.

A reliable stabilization of the two adjacent vertebral bodies relative to one another is preferably achieved in that the stabilizing element is introduced in such a manner that it passes through the one, in particular the superior one, of the two adjacent vertebral bodies and that one end of the stabilizing element comes to rest in the other, in particular the inferior one, of the two adjacent vertebral bodies.

The stabilizing element is preferably introduced in such a manner that it comes to lie on a connection line between a pedicle of the superior one of the two adjacent vertebral bodies and between a point in the inferior third of the anterior edge of a sagittal section of the inferior one of the two adjacent vertebral bodies, or that it comes to lie on a connection line between a pedicle of the inferior one of the two adjacent vertebral bodies and between a point in the superior third of the anterior edge of a sagittal section of the superior one of the two adjacent vertebral bodies. The stabilizing element connects the two vertebral bodies thereby in a reliable manner and can be introduced through a single access point.

The stabilizing element is preferably introduced in such a manner that it lies, when viewed from the dorsal in the sagittal direction, on a line that has an entrance point between 9 and 11 o'clock and an exit point between 4 and 6 o'clock on a pedicle clock of the superior vertebral body, or that has an entrance point between 1 and 3 o'clock and an exit point between 6 and 8 o'clock on a pedicle clock of the superior vertebral body, or that has an entrance point between 7 and 9 o'clock and an exit point between 12 and 2 o'clock on a pedicle clock of the inferior vertebral body, or that has an entrance point between 3 and 5 o'clock and an exit point between 10 and 12 o'clock on a pedicle clock of the inferior vertebral body. This position of the stabilizing element achieves a reliable stabilization of the two vertebral bodies relative to one another.

The stabilizing element is preferably introduced along a guide wire, which facilitates the positioning of the stabilizing element.

According to a preferred environment of the invention, the relative position of the two adjacent vertebral bodies can be varied relative to one another by the stabilizing element, which can bring about a desired stabilization of the vertebral column in a simple manner.

The stabilizing element is preferably constructed as a bone screw that can be introduced in an especially simple manner and finds a good hold in the vertebral bodies by the threading.

The bone screw is advantageously inserted into a casing that has a section with an outer threading. The casing brings about an additional stabilization of the bone screw in the vertebral body.

The bone screw is especially preferably inserted into a casing that has a front section, a middle section and a rear section, whereby the front section has an outer threading and at least one spreading element is arranged in the middle section. After the insertion of the casing, the spreading elements can be spread open in order to stabilize, for example, straighten out one of the vertebral bodies through which the casing is guided.

According to a preferred embodiment of the invention, an intervertebral disk prosthesis is inserted between the two adjacent vertebral bodies through which prosthesis the stabilizing element passes. In this manner, an additional stabilization of the vertebral column can be achieved and in particular a stabilization of the intervertebral disk prosthesis and the bone screw relative to one another can be achieved.

The intervertebral disk prosthesis is especially preferably constructed substantially U-shaped with a first shank and a second shank, whereby the two shanks can be pivoted relative to one another. This makes possible a minimally invasive introduction of the intervertebral disk prosthesis. In particular, at first the intervertebral disk prosthesis and subsequently the bone screw can be inserted, or also at first the bone screw and subsequently the intervertebral disk prosthesis can be inserted.

The process in accordance with the invention for introducing an intervertebral disk prosthesis into an intervertebral space between two adjacent vertebral bodies is distinguished in that the intervertebral disk prosthesis is introduced through a single extraforaminal access point. Thus, the access point lies further dorsally, however, at such a large angle to the sagittal plane that the access is not guided through the foramen but rather an introduction of the intervertebral disk prosthesis into the intervertebral space is laterally possible (cf. FIG. 49). A damaging of the foramen and a significant trauma to the soft tissue of the patient are therefore avoided. This operation procedure is therefore designated as EFOLIF (extraforaminal interbody fusion).

Nerve roots present between the extraforaminal access point and the intervertebral space are pressed either inferior-medially or superior-laterally. If the nerve roots are pressed inferior-medially, or cauda-dorsally, the operation procedure is designated as EPAPINLIF (extraforaminal parapedicular inferior interbody fusion), whereas the operation procedure in which the nerve roots are pressed superior-laterally or ventro-cranially is designated as EPAPSULIF (extraforaminal parapedicular superior interbody fusion).

According to an advantageous further development of the intervertebral a first fixation screw is introduced through the extraforaminal access point transpedicularly or extrapedicularly. This eliminates further accesses for the introduction of fixation screws for fastening a rod system.

A second fixation screw is preferably introduced through the extraforaminal access point extrapedicularly. This eliminates further accesses for the introduction of fixation screws for fastening a rod system.

An advantageous environment of the invention provides that the first fixation screw is attached to the inferior one of the two adjacent vertebral bodies and that the second fixation screw is attached to the superior one of the two adjacent vertebral bodies, and that a rod is fastened to the first fixation screw and to the second fixation screw. This makes it possible to introduce the intervertebral disk prosthesis through a single access as well as the fastening of a rod system.

BRIEF DESCRIPTION OF THE DRAWINGS

The invention is explained in detail using the following figures:

FIG. 1b shows a lateral view of the two vertebral bodies according to FIG. 1a.

FIG. 2b shows a top view onto the two virtual bodies in accordance with FIG. 2a.

FIG. 3 shows a perspective view of a first exemplary embodiment of a casing.

FIG. 3a shows a top view onto the rear end of the casing according to FIG. 3;

FIG. 4 shows the casing according to FIG. 3 with a screw to be introduced therein.

FIG. 5 shows the casing according to FIG. 3 with a screw set therein.

FIG. 6 shows the casing according to FIG. 3 with a screwing-in instrument sets on it.

FIG. 7 shows a perspective view of a second exemplary embodiment of a casing.

FIG. 8 shows the casing according to FIG. 7 in the spread-open state.

FIG. 9 shows a lateral view of the casing according to FIG. 7.

FIG. 10 shows a sectional enlargement of the casing according to FIG. 7.

FIG. 11 shows a lateral view of a third exemplary embodiment of a casing.

FIG. 12 shows the casing according to FIG. 11 in partial section.

FIG. 13 shows a top view onto the rear end of the casing according to FIG. 11,

FIG. 14 shows the casing according to FIG. 11 in a partially screwed-in-state.

FIG. 15 shows the casing according to FIG. 11 in the screwed-in-state.

FIG. 16 shows another view of the casing according to FIG. 15.

FIG. 17 shows a longitudinal section through the casing according to FIG. 11.

FIG. 59 shows the screw according to FIG. 57, onto which the casing according to FIG. 57 is screwed on.

In the figures, the same reference numerals designate parts that are identical or identical in nature. For the sake of clarity, not all reference numerals are indicated in all figures.

DETAILED DESCRIPTION OF THE PREFERRED EMBODIMENTS

FIGS. 1a, 1b and 2a, 2b show two adjacent vertebral bodies 100, 200, whereby vertebral body 100 forms the superior vertebral body and vertebral body 200 forms the inferior vertebral body. An intervertebral space 250 is arranged between the two vertebral bodies 100, 200. In order to be able to reestablish the stability of the vertebral column, for example, in the case of a defective intervertebral disk, in many operation procedures the two adjacent vertebral bodies 100, 200 and are rigidly connected to one another. According to the process in accordance with the invention, the connection of the two adjacent vertebral bodies 100, 200 takes place by means of a stabilizing element that directly connects the two adjacent vertebral bodies 100, 200 to one another. The connection takes place in particular in such a manner that the stabilizing element passes through each of the two adjacent vertebral bodies 100, 200 in the longitudinal direction of the vertebral column at least in sections so that in particular rod systems with several components arranged on the back side of vertebral bodies 100, 200 are avoided.

Figure 1B:
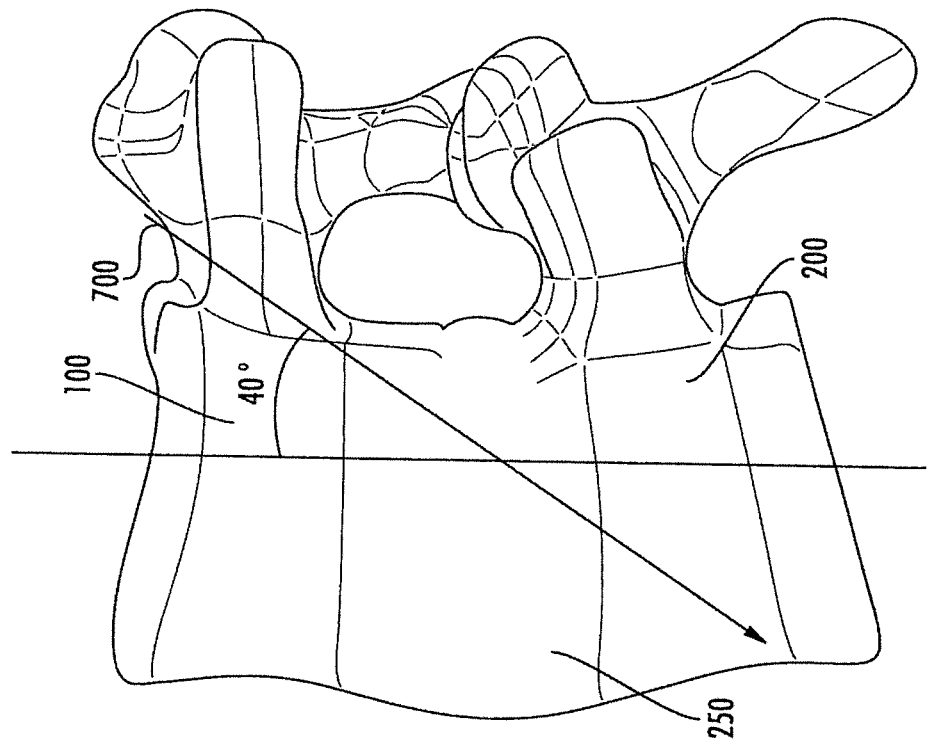
Figure 1A:
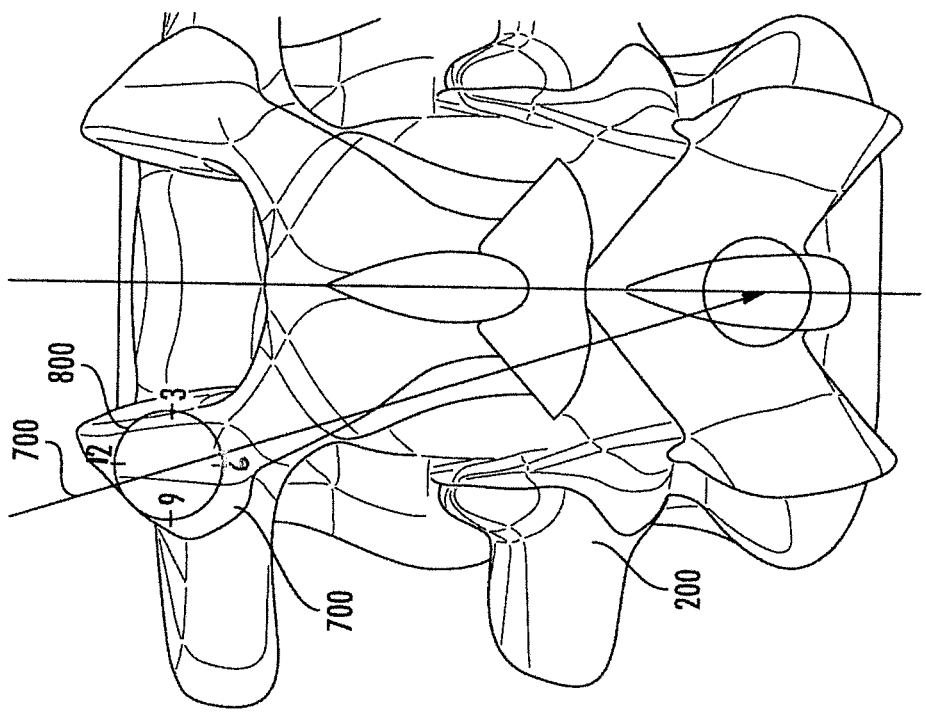
FIG. 1a shows a front view of two adjacent vertebral bodies.

The stabilizing element is introduced in a first alternative along connection line 700 shown in FIGS. 1a and 1b. In this alternative, the introduction takes place from the cranial to the caudal. The introduction is possible through a single access point arranged in particular dorso-medially. As can be recognized, in particular in FIG. 1b, connection line 700 runs between a pedicle of superior vertebral body 100 and a point in the inferior, alternatively also in the superior, third of the anterior edge of a sagittal section of the inferior vertebral body 200. The sagittal section does not have to run symmetrically through the vertebral bodies 100, 200 but rather can also run parallel to them in an offset manner. As can be recognized in FIG. 1, connection line 700 has an entrance point between 9 and 11 o'clock and an exit point between 4 and 6 o'clock viewed dorsally in the sagittal direction on a pedicle clock 800 of superior vertebral body 100. Of course, the stabilizing element can also be introduced mirror-symmetrically to the sagittal plane and thus connection line 700 has an entrance point between 1 and 3 o'clock and an exit point between 6 and 8 o'clock on a pedicle clock of superior vertebral body 100. A clock arranged in an imaginary manner on a pedicle is considered as pedicle clock 800, which can be recognized in a front view and whose connection line runs between its 12 and its 6 approximately parallel to the longitudinal axis of the vertebral column.

If a stabilizing element is introduced along connection line 700, it passes at first through superior vertebral body 100 until a distal end of the stabilizing element comes to lie in inferior vertebral body 200, so that the two vertebral bodies 100, 200 can be directly connected to one another by the stabilizing element in this manner.

In order to be able to insert the stabilizing element, at first the point on superior vertebral body 100 is determined on which the imaginary pedicle clock 800 is arranged, and the alignment of connection line 700 is determined. A bearing is taken on the pedicle on which connection line 700 enters into superior vertebral body 100 in particular in the anterior-posterior beam path and on the vertebral spine of inferior vertebral body 200. At first, a guide wire is introduced along connection line 700. Finally, the stabilizing element is introduced along the guide wire.

Figure 2B:
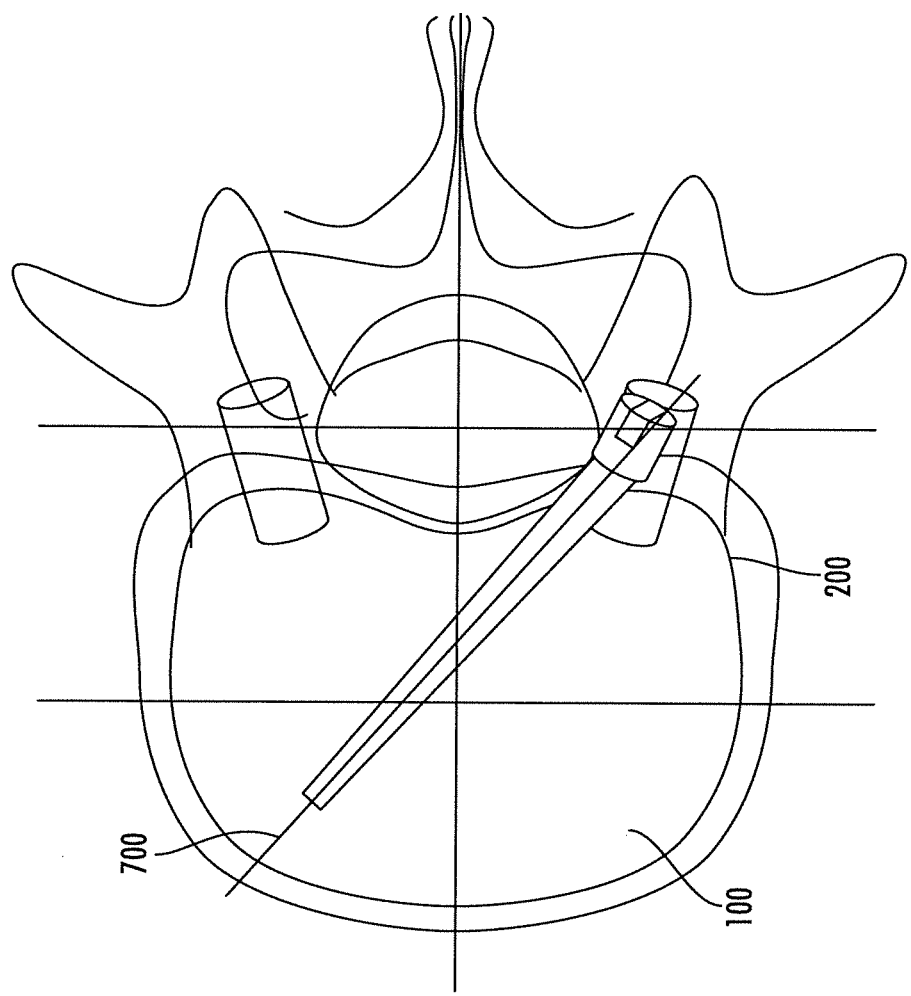
Figure 2A:
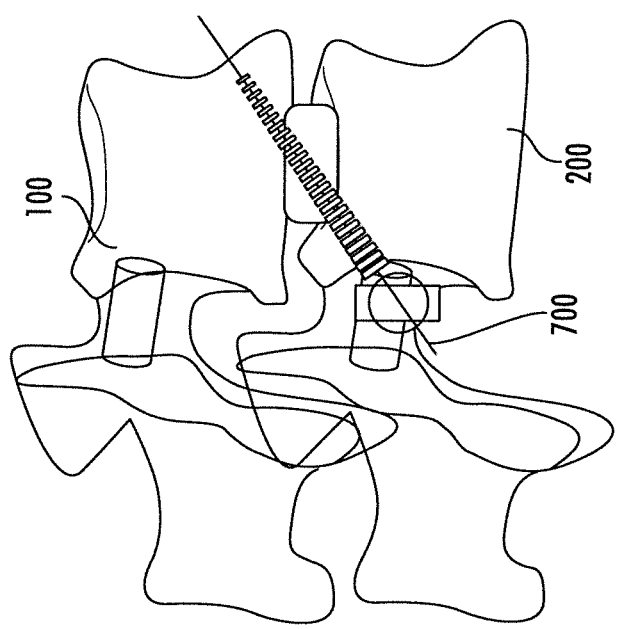
FIG. 2a shows a lateral view of two adjacent vertebral bodies.

The stabilizing element is introduced in a second alternative along connection line 700' shown in FIGS. 2a and 2b. In this alternative the introduction takes place from caudal to cranial. The introduction is possible through a single access point that is arranged in particular dorso-medially. As can be recognized in particular in FIG. 2a, connection line 700' runs between a pedicle of inferior vertebral body 200 and a point in the inferior, alternatively also in the superior, third of the anterior edge of a sagittal section of superior vertebral body 200. The sagittal section does not have to run symmetrically through vertebral bodies 100, 200 but rather can also run parallel to them in an offset manner. Connection line 700' has an entrance point between 7 and 9 o'clock and an exit point between 12 and 2 o'clock when viewed from the dorsal in the sagittal direction on a pedicle clock of inferior vertebral body 200. Of course, the stabilizing element can also be introduced mirror-symmetrically to the sagittal plane and thus connection line 700 has an entrance point between 3 and 5 o'clock an exit point between 10 and 12 o'clock on a pedicle clock of the inferior vertebral body.

If a stabilizing element is introduced along connection line 700', it passes at first through inferior vertebral body 200 until a distal end of the stabilizing element comes to lie in superior vertebral body 100, so that in this manner the two vertebral bodies 100, 200 are directly connected to one another by the stabilizing element.

In order to be able to insert the stabilizing element, at first the point on the inferior vertebral body 200 is determined at which imaginary pedicle clock 800 is arranged and the alignment of connection line 700' determined. A bearing is taken on the pedicle at which connection line 700' enters into inferior vertebral body 200, in particular in the anterior-posterior beam path, and on the vertebral spine of superior vertebral body 100. At first, a guide wire is introduced along connection line 700.' Finally, the stabilizing element is introduced along the guide wire.

Figure 49:
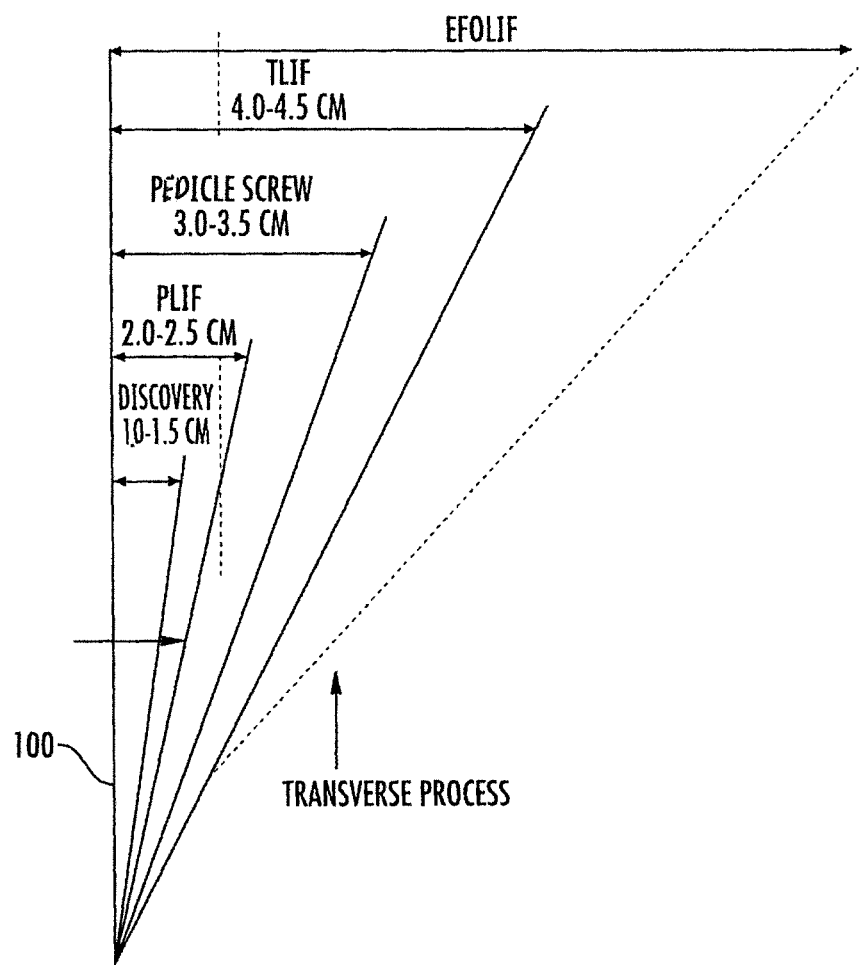
FIG. 49 shows a schematic view of different access paths.
Figure 50:
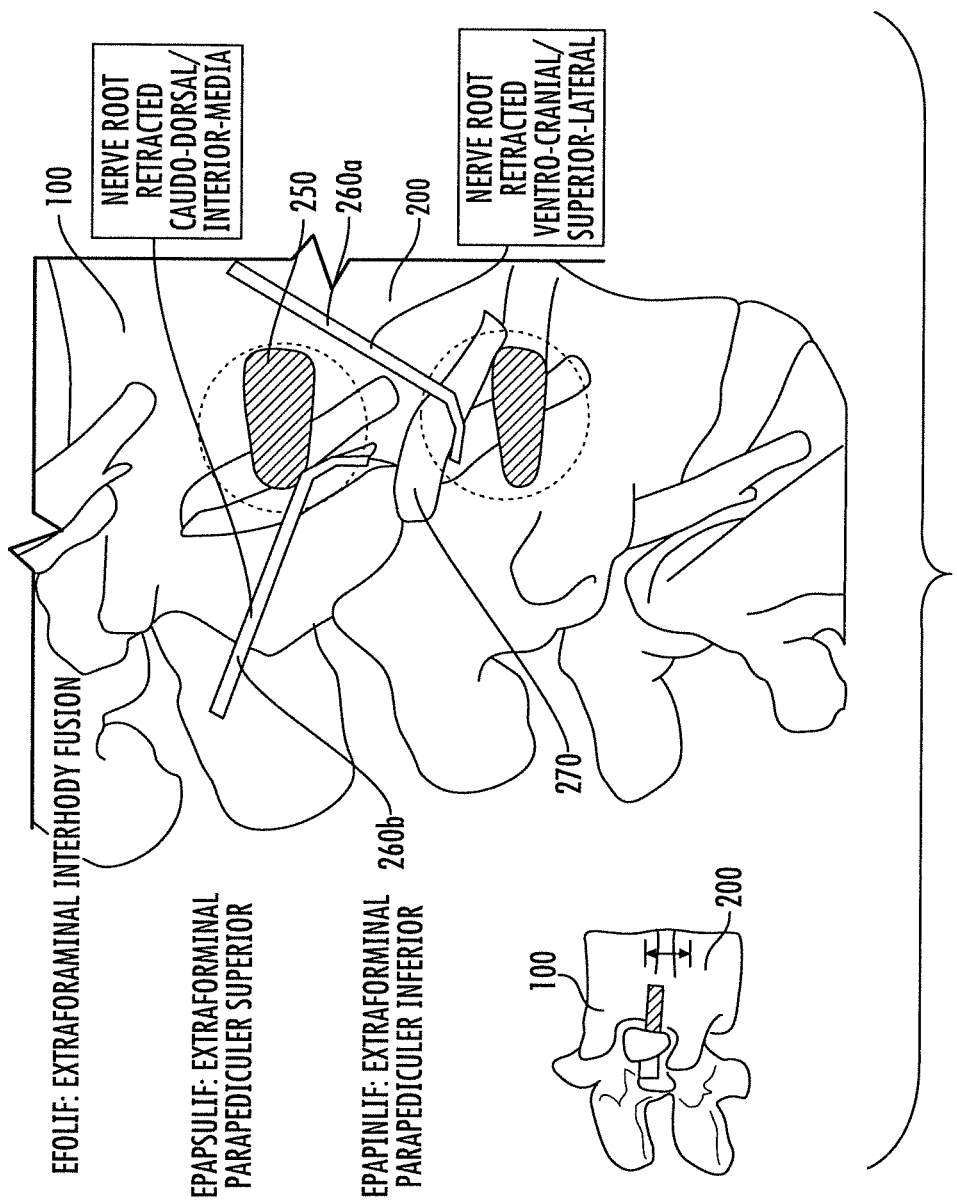
FIG. 50 shows a schematic view of the extraforaminal access path.
Figure 51:
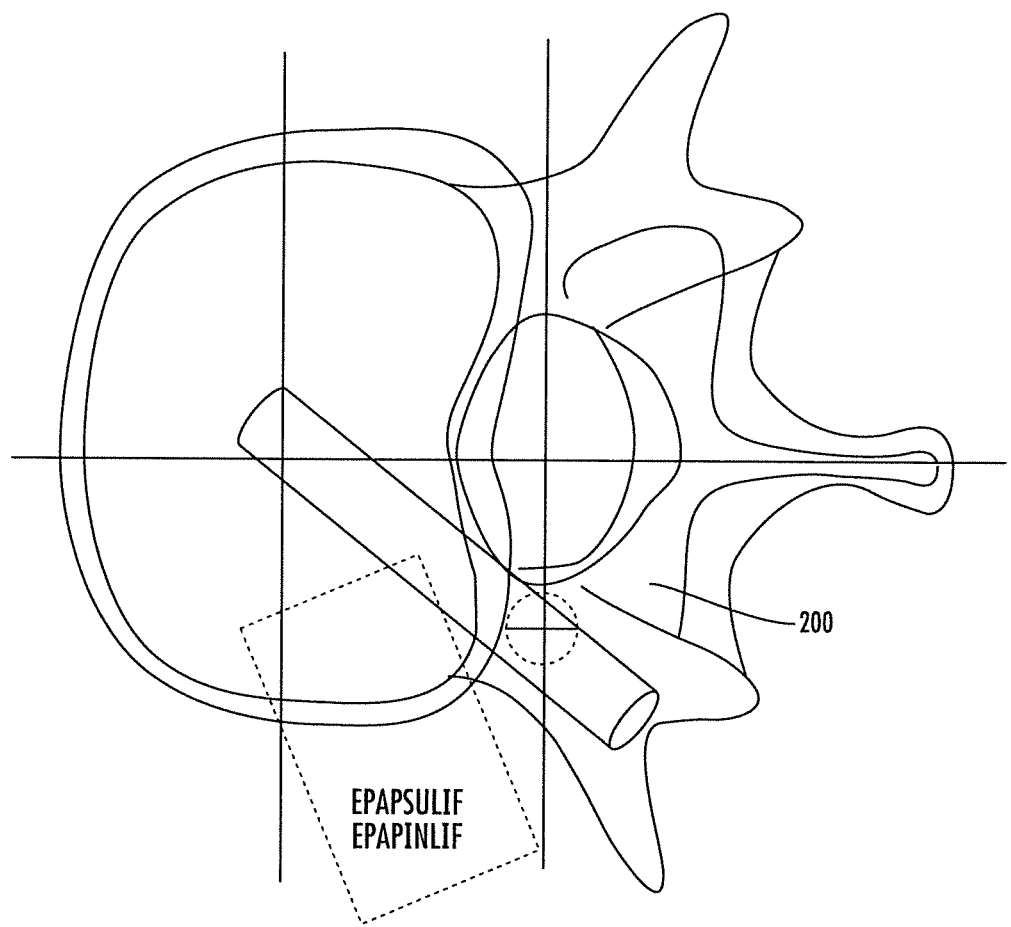
FIG. 51 shows another schematic view of the extraforaminal access path.

Alternatively, or additionally, to the stabilizing element that is used, in particular in accordance with one of the two previously described processes, an intervertebral disk prosthesis can be used. This takes place via an operation procedure in accordance with the invention in which the intervertebral disk is introduced through a single extraforaminal access point. The access point is therefore located further dorsally, but at such a large angle to the sagittal plane that the access is not guided through the foramen but rather an introduction of the intervertebral disk prosthesis into intervertebral space 250 is laterally possible (cf. FIGS. 49 and 51). The intervertebral disk prosthesis can be laterally introduced from the right as well as from the left. This avoids damage to the foramen and severe trauma to the soft tissue of the patient. This operation process is therefore designated as EFOLIF (extraforaminal interbody fusion). Nerve roots present between the extraforaminal access point and intervertebral space 250 are pressed either inferior-medially or superior-laterally. This is shown in particular in FIG. 50. A surgical instrument 260a is used to press a nerve root 270 arranged between the access point and intervertebral space 250 superior-laterally or, expressed another terms, ventro-cranially. This operation procedure is designated as epapsulif (extraforaminal parapedicular superior interbody fusion). A surgical instrument 260b is used to press a nerve root 270 arranged between the access point and intervertebral space 250 alternatively inferior-medially or, expressed another terms, caudo-dorsally. This operation procedure is designated as EPAPINLIF (extraforaminal parapedicular inferior interbody fusion). The intervertebral disk prosthesis can be introduced laterally into intervertebral space 250 in the EPAPINLIF process as well as in the EPAPSULIF process (cf. FIG. 51) without damaging the forearm and as in traditional transforaminal processes.

Figure 52:
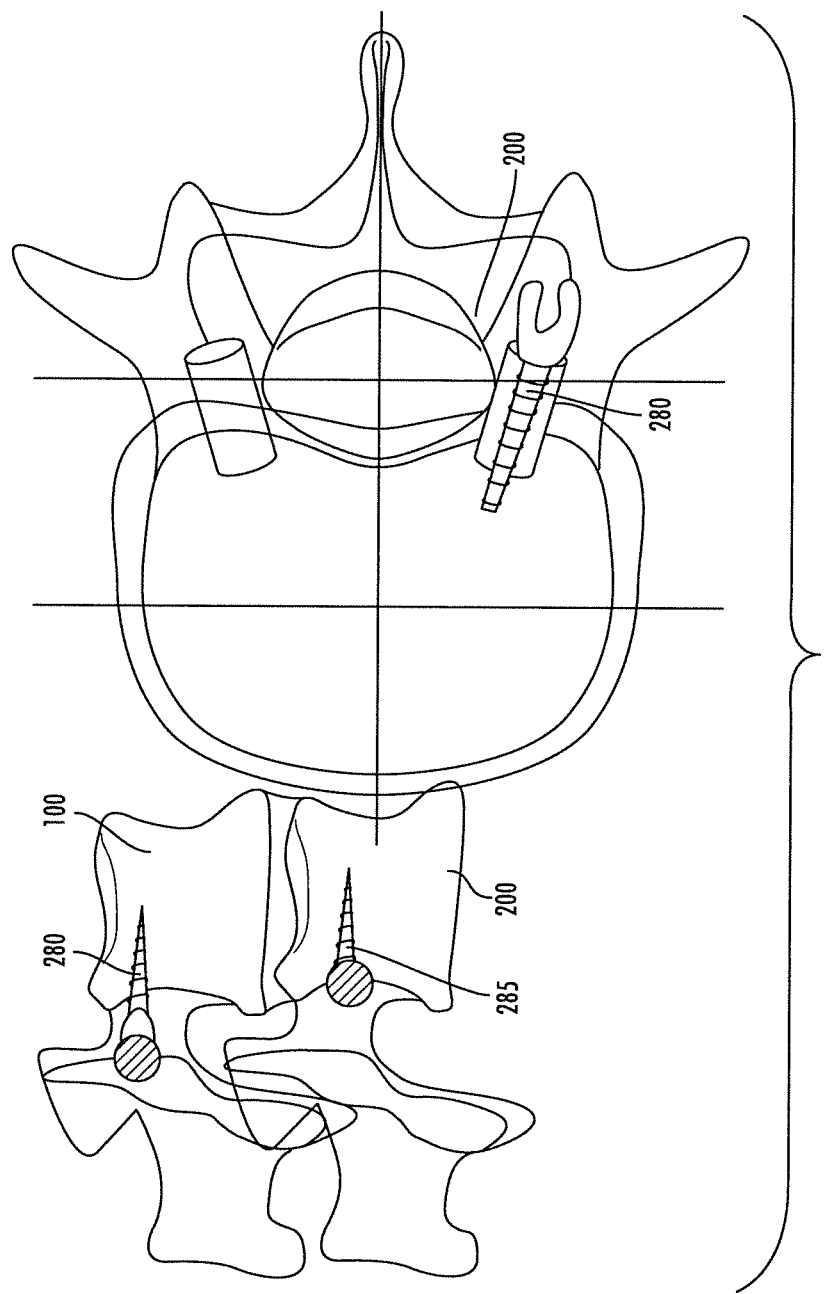
FIG. 52 shows a schematic view of the vertebral body with attached first fixation screw.
Figure 53:
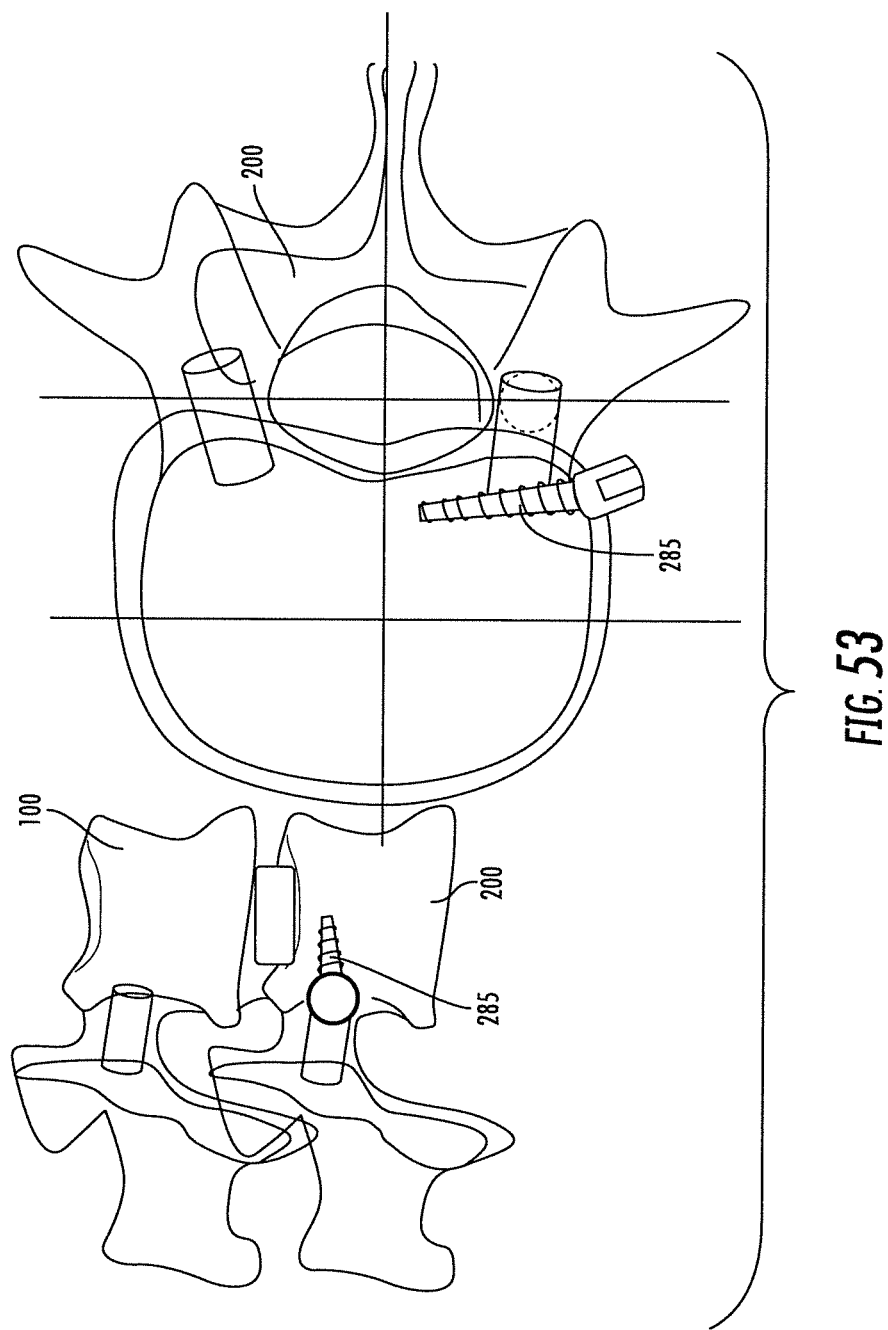
FIG. 53 shows a schematic view of the vertebral body with an attached second fixation screw.
Figure 54A:
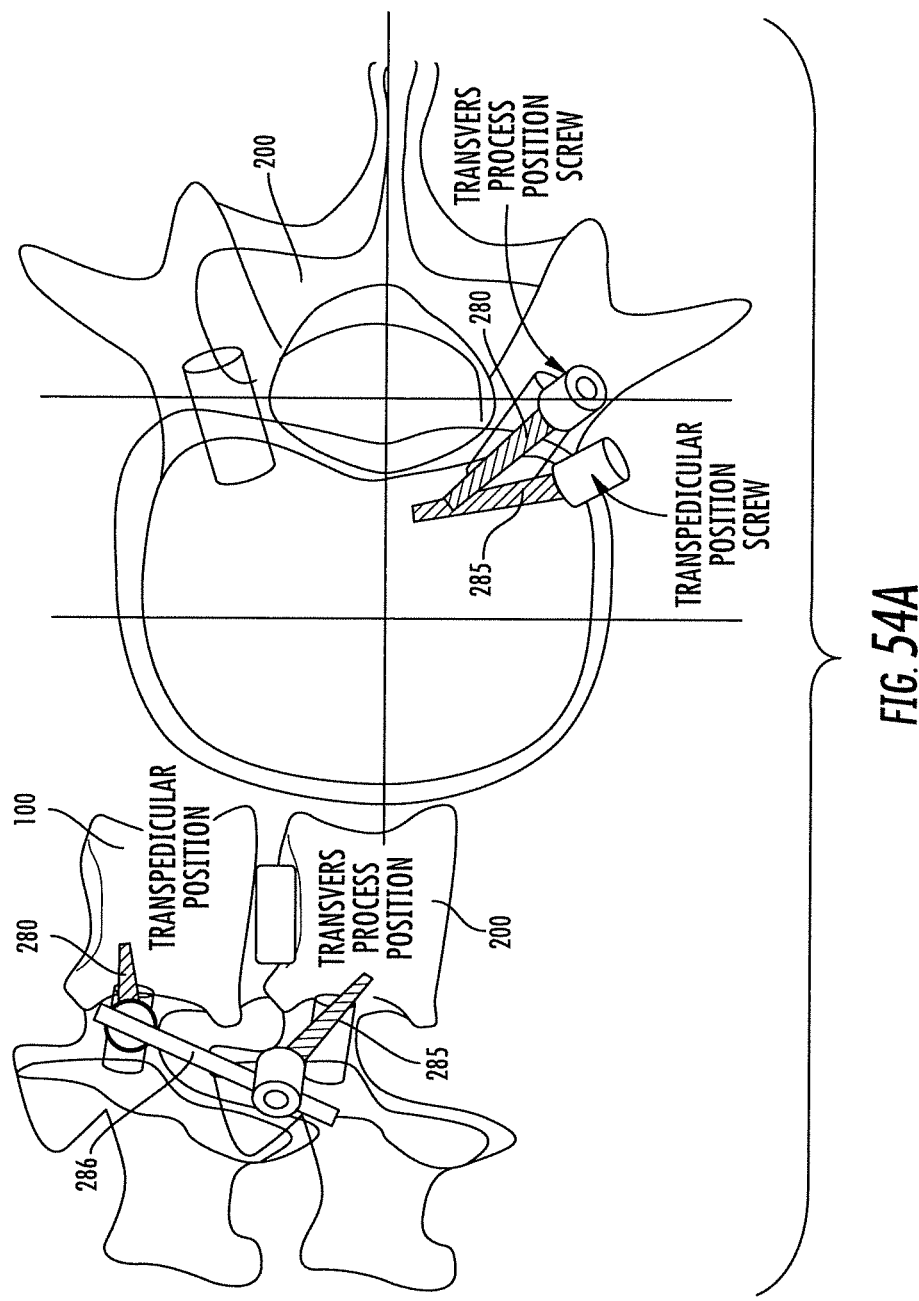
FIG. 54a shows a schematic view of the vertebral body with attached rod.
Figure 54B:
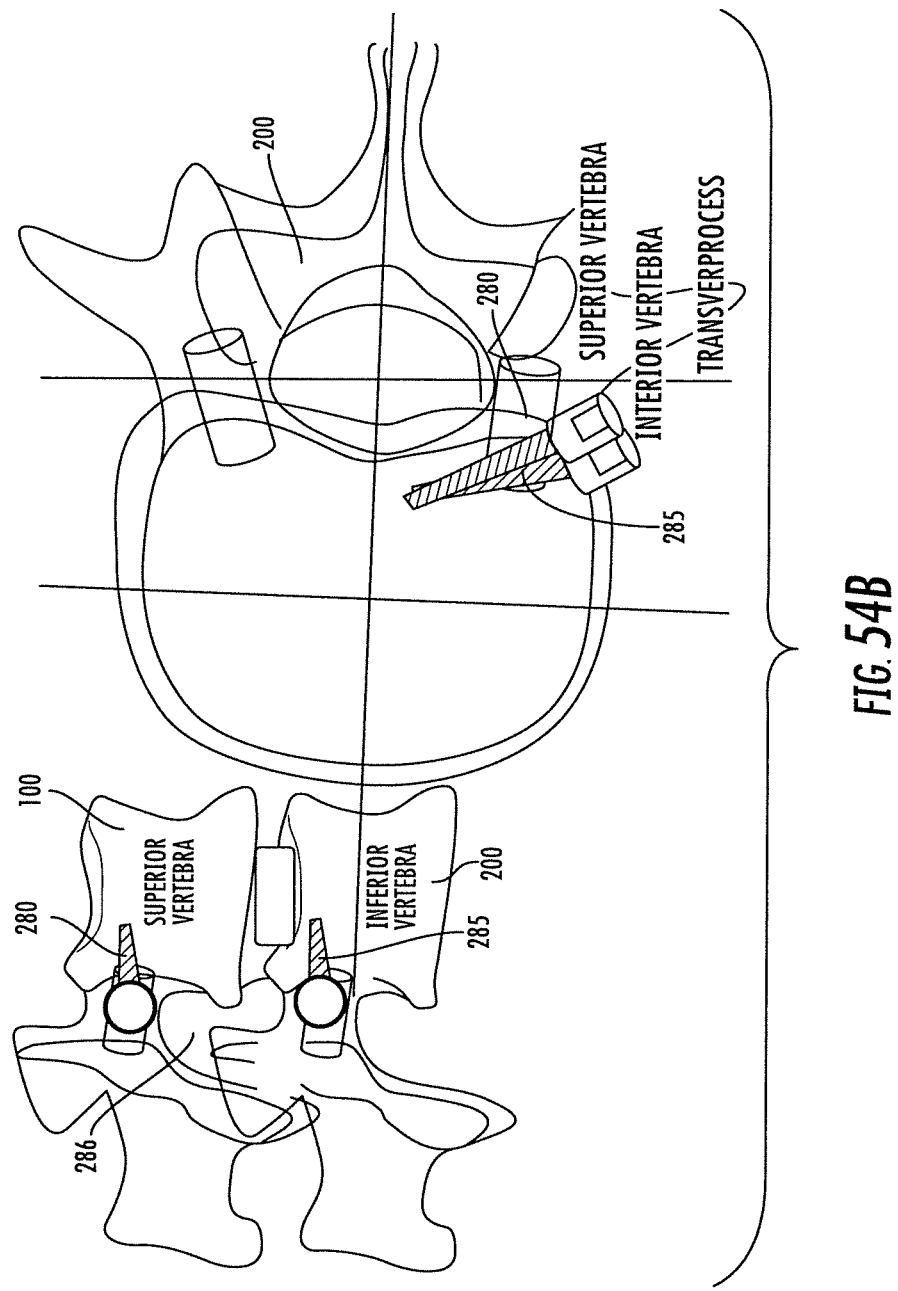
FIG. 54b shows a schematic view of the vertebral body with attached rod with the first fixation screw in an alternative position.

In addition, the extraforaminal access point through which the intervertebral disk prosthesis is introduced also makes possible an introduction of a rod system if the intervertebral disk prosthesis is not to be used in combination with the previously described stabilizing element that directly connects the two adjacent vertebral bodies 100, 200 to one another. In order to fasten the rod system, a first fixation screw 280 is introduced transspedicularly, i.e., through a pedicle of the vertebral body, in particular of superior vertebral body 100, through the extraforaminal access point (FIG. 52). Furthermore, a second fixation screw 285 is introduced extrapedicularly, i.e., not through the pedicle, but rather transversely to the pedicle through the extraforaminal access point, in particular into inferior vertebral body 200 (cf. FIG. 53). Fixation screws 280, 285 are designed in such a manner that a rod can be attached to their heads so that after the introduction of fixation screws 280, 285 a rod 286 is fastened to the first fixation screw 280 and to the second fixation screw 285 for a rigid connection of the two adjacent vertebral bodies 100, 200 (cf. FIG. 54a). Alternatively, as shown in FIG. 54b, the first fixation screw 280 can also be fastened extrapedicularly in superior vertebral body 100 (cf. FIG. 54b).

Embodiments of the stabilizing element are described in the following.

FIGS. 3 to 6 show different views of a first exemplary embodiment of a casing 10 with a front section 11, a central area 12 following it and with a following rear area 13. Front area 11 carries an outer threading 14. Rear area 13 is designed smooth on its outer side or optionally structured in the longitudinal direction. Several slots 15 are arranged in the central area in the longitudinal direction of casing 10 between which spreading elements 16 are formed. In the present instance, slots 15 are arranged regularly distributed over the circumference. A total of four spreading elements 16 are formed; however, the number of spreading elements 16 can also be higher or lower. In particular, spreading elements 16 can also be arranged and formed asymmetrically over the outer circumference of casing 10.

A first inner threading is arranged in front area 11 of casing 10 which spreading has a first pitch. A screw 20 can be screwed into casing 10, in particular into the first inner threading of casing 10, which screw has a shaft 20*a* and a head 20*b*. Shaft 20*a* has a front section 21, a following central area 22 and rear section 23 following the latter, whereby head 20*b* follows rear section 23. A first outer threading 24 is arranged in front section 21 of screw 20 whereas a second outer threading 25 is arranged in rear section 23. The first outer threading 24 has a third pitch whereas the second outer threading 25 has a fourth pitch. However, the third pitch of first outer threading 24 corresponds in particular to the first pitch of the first inner threading of casing 10. The third pitch and the fourth pitch are selected differently so that screw 20 acts as a traction screw or compression screw. When screw 20 is screwed into casing 10, as is apparent in particular in FIG. 5, the first section 11 is drawn against rear section 13 by the different pitches of the first and second outer threadings 24, 25, whereby spreading elements 16 arranged in the central range spread radially outward. Spreading elements 16 have set kinks 17 that are intended to ensure a defined spreading open of spreading elements 16.

Casing 10 can also have only front section 11 with outer threading 14 without the following central and rear areas 12, 13 (not shown) in order to bring about a stabilization of screw 20 in the vertebral body.

Figure 18:
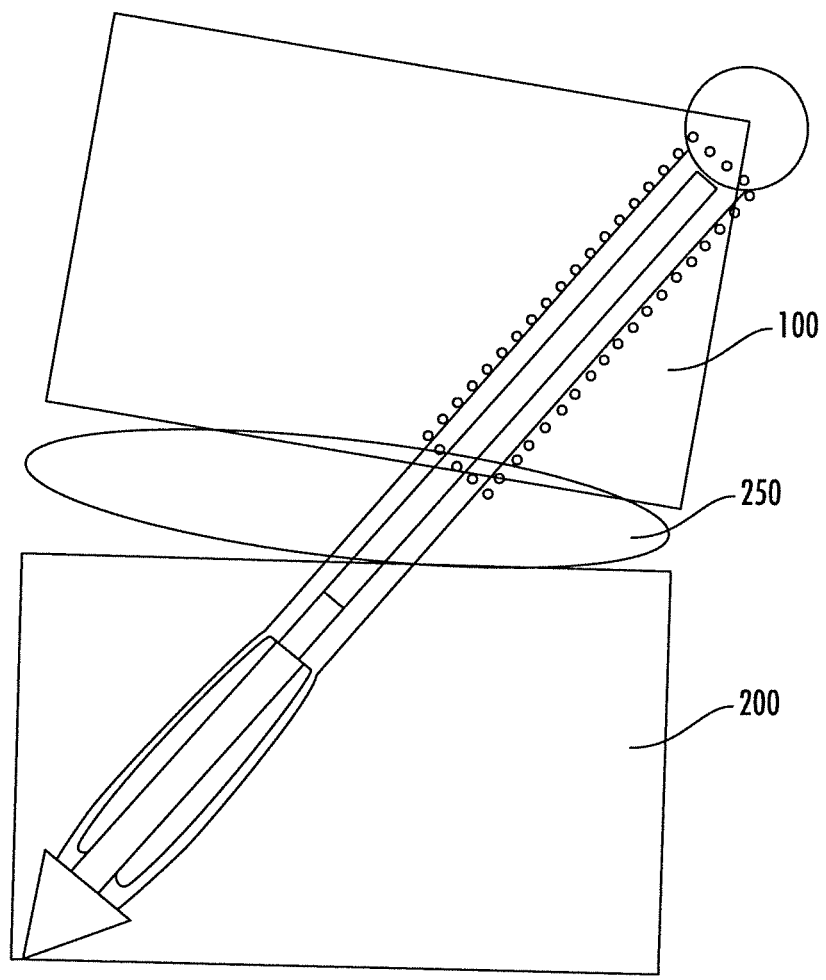
FIG. 18 shows a schematic view of the casing according to FIG. 3 in a state inserted in a vertebral body.

A screwdriver instrument 40 is used to insert casing 10 into vertebral bodies 100, 200 (cf. FIG. 18). Casing 10 has an out-of-round contour 18 on its one end, especially on the free end of rear section 13 (cf. FIG. 3*a*), in which contour a correspondingly formed contour of screwdriver instrument 40 engages in order to screw the casing into vertebral bodies 100, 200. As is apparent from FIG. 18, in which two adjacent vertebral bodies 100, 200 are schematically shown with an intervertebral space 250 between them, casing 10 is screwed in through upper vertebral body 100 until into lower vertebral body 200, whereby casing 10 passes through intervertebral space 250. Central area 12 with spreading elements 16 comes to rest inside lower vertebral body 200. If screw 20 is subsequently screwed in, spreading elements 16 spread open inside vertebral body 52 in order, for example, to straighten it out and stabilize it.

A stop 26 is arranged on screw shaft 20*a*, in particular between central area 22 and rear area 23 of screw 20, against which stop the free end of rear area 13 of casing 10 strikes during the screwing in of screw 20 so that front area 11 of casing 10 can be drawn against rear area 13 of casing 10 and spreading elements 16 spread open in central area 12.

Screw 20 is cannulized so that during the implantation a guide wire 30 can be introduced at first via which easing 10 and finally screw 20 can subsequently be introduced.

FIGS. 7 to 10 show another exemplary embodiment of a casing 10' that can be inserted without a screw. Casing 10' is manufactured from a memory metal, in particular nitinol, which changes its form in particular upon reaching the body temperature. Casing 10' has slots 15 also running in the longitudinal direction between which spreading elements 16 are formed. After casing 10' has been inserted into vertebral bodies 100, 200 and the body temperature reached, front section 11 and rear section 13 move relatively toward one another so that spreading elements 16 are spread open in central area 12 (cf. FIG. 8). Casing 10' is stabilized thereby in vertebral body 200 via outer threading 14 of front area 11.

A third exemplary embodiment of a casing 10" is shown in FIGS. 11 to 16. Casing 10" has slots 15" that extend in the longitudinal direction but run at an incline to the longitudinal direction. If front area 11 and rear area 13 are moved toward one another and in particular are rotated relative to one another at this time, spreading elements 16 formed between slots 15" spread open, whereby they remain almost resting on one another in particular during the rotation of front section 11 against rear section 13 and form a circumferential bead (cf. FIG. 15).

Figure 19:
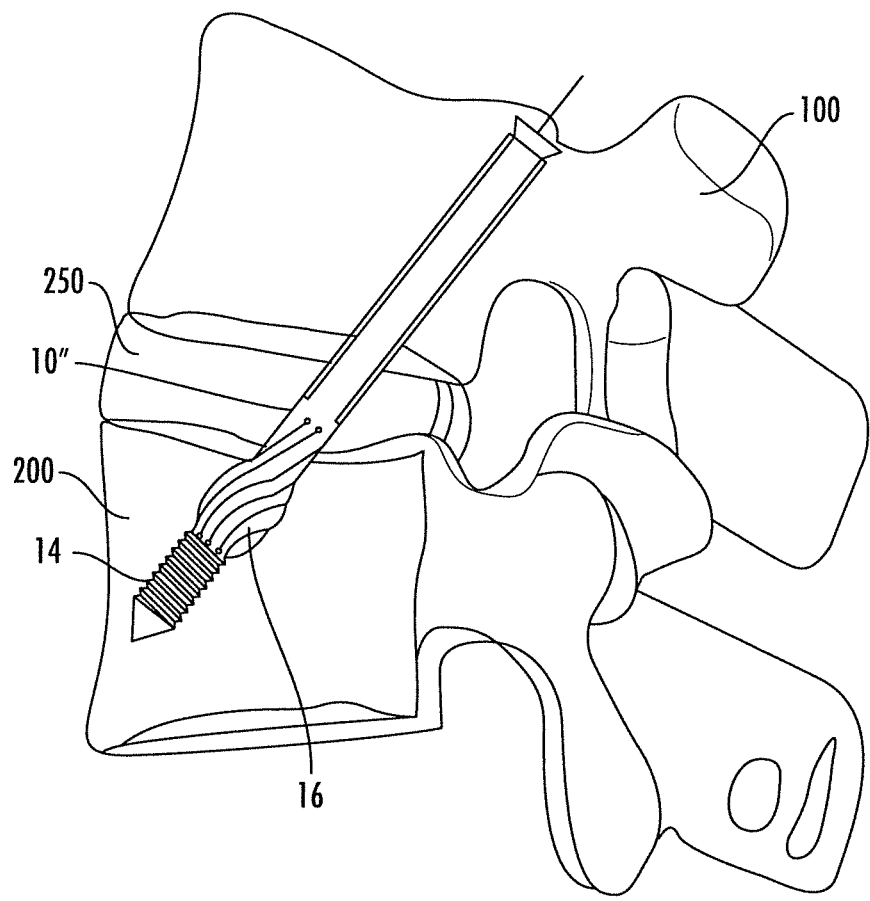
FIG. 19 shows a schematic view of the casing according to FIG. 11 in a state inserted in a vertebral body.
Figure 20:
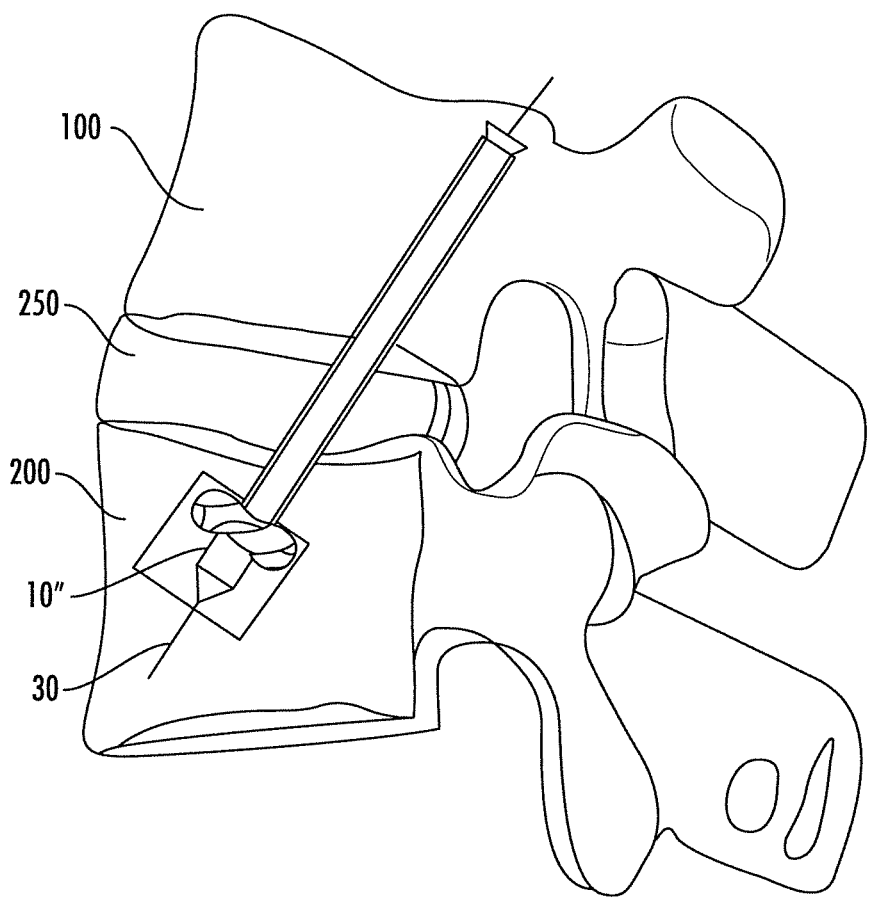
FIG. 20 shows the casing according to FIG. 19 in a state screwed further into a vertebral body.
Figure 21:
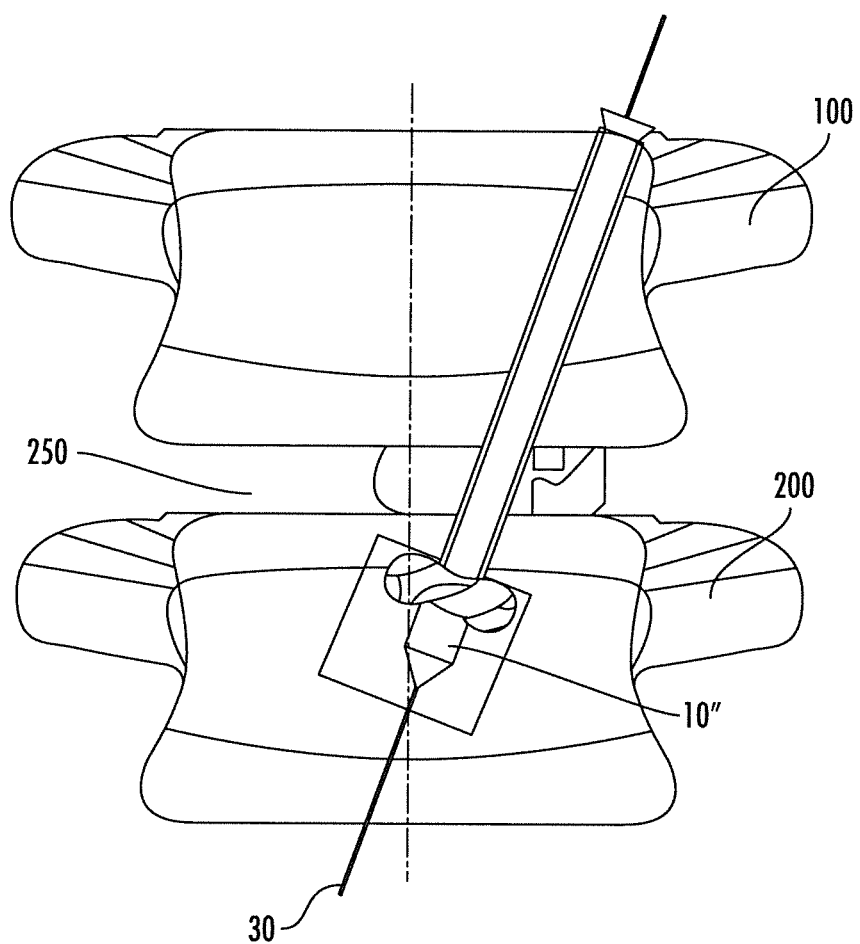
FIG. 21 shows a front view of the casing according to FIG. 20 in a state inserted in a vertebral body.

FIGS. 19 to 21 show how casing 10' comes to rest in the adjacent vertebral bodies 100, 200. Casing 10' is introduced through upper vertebral body 100, passes through intervertebral space 250 and is introduced so far that front area 11 and central area 12 come to rest in lower vertebral body 200. Spreading elements 16 stabilize lower vertebral body 200 after the spreading open of casing 10'.

The stabilizing element can therefore be formed from a casing such as, for example, casing 10 or 10' in combination with a bone screw, for example, bone screw 20, or solely from one casing such as, for example, casing 10", or also solely from one bone screw such as, for example, bone screw 20.

If the stabilizing element is formed exclusively by a bone screw, the bone screw can have a pitch over its entire length. In a preferred embodiment of the invention, bone screw 20 has a shaft 20*a* and a head 20*b*, which shaft 20*a* has a front section 21, a following central area 22 and following rear section 23, which rear section 23 is followed by head 20*b* (cf. FIG. 4). A first outer threading 24 is arranged in front section 21 of screw 20 whereas a second outer threading 25 is arranged in rear section 23. First outer threading 24 has a third pitch, whereas second outer threading 25 has a fourth pitch. The third pitch and the fourth pitch are selected differently so that screw 20 acts as a traction screw or compression screw by means of which the relative position of the two adjacent vertebral bodies 100, 200 can be varied relative to one another.

Figure 55:
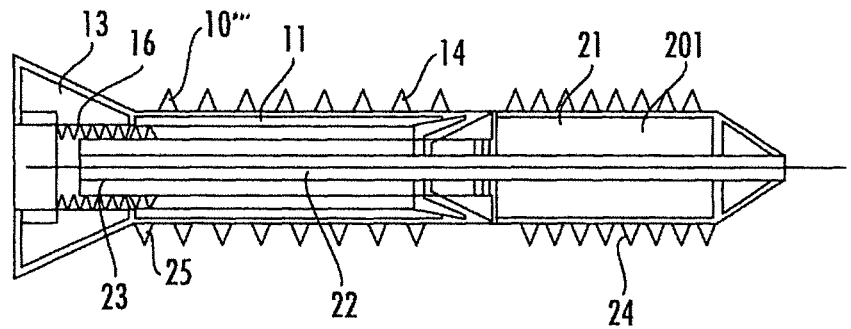
FIG. 55 shows a side view of a fourth exemplary embodiment of a casing with a screw inserted in it.
Figure 56:
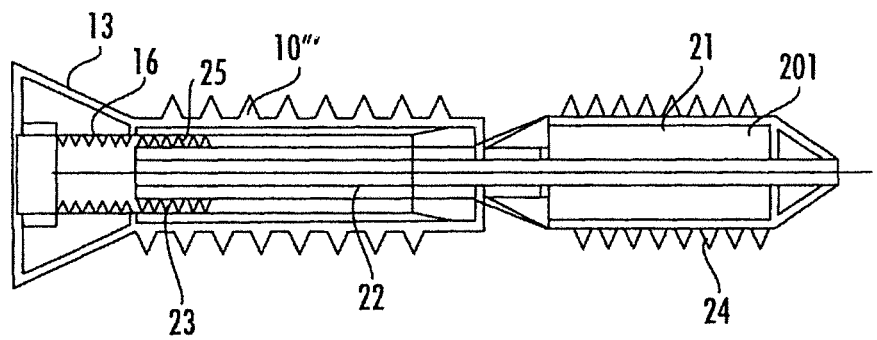
FIG. 56 shows the casing according to FIG. 55 with an only partially inserted screw.
Figure 57:
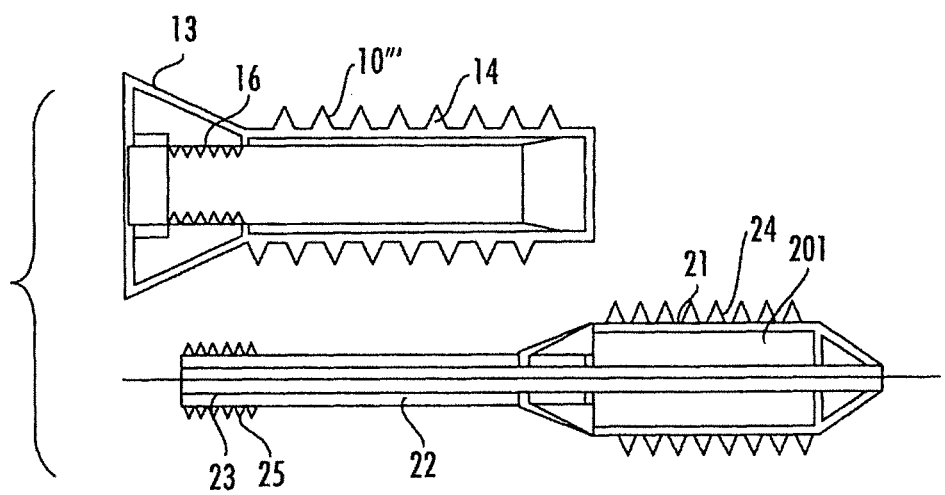
FIG. 57 shows the casing according to FIG. 55 with the screw according to FIG. 55.
Figure 58:
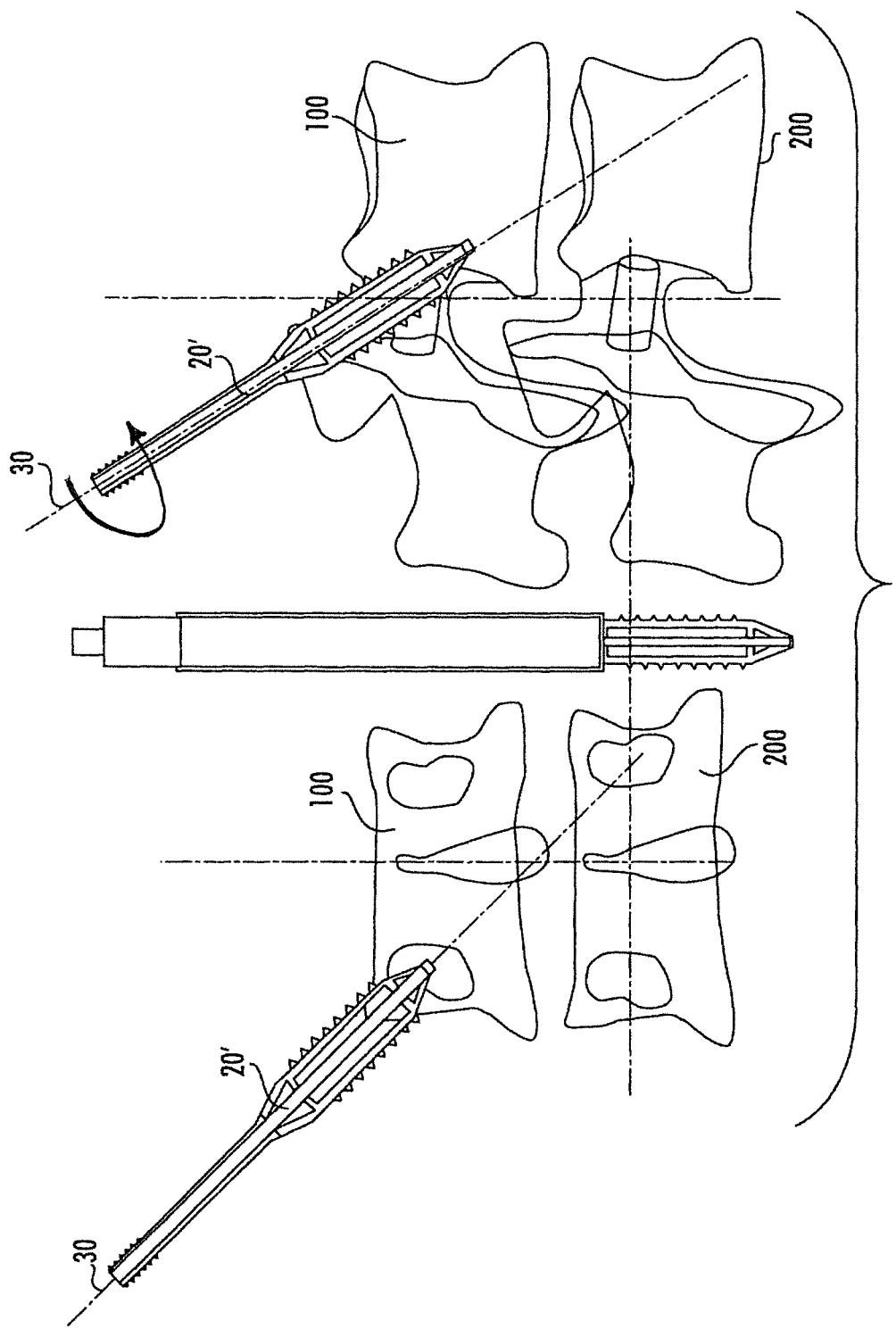
FIG. 58 shows a schematic view of the screw according to FIG. 57 in a state inserted into a vertebral body.
Figure 59:
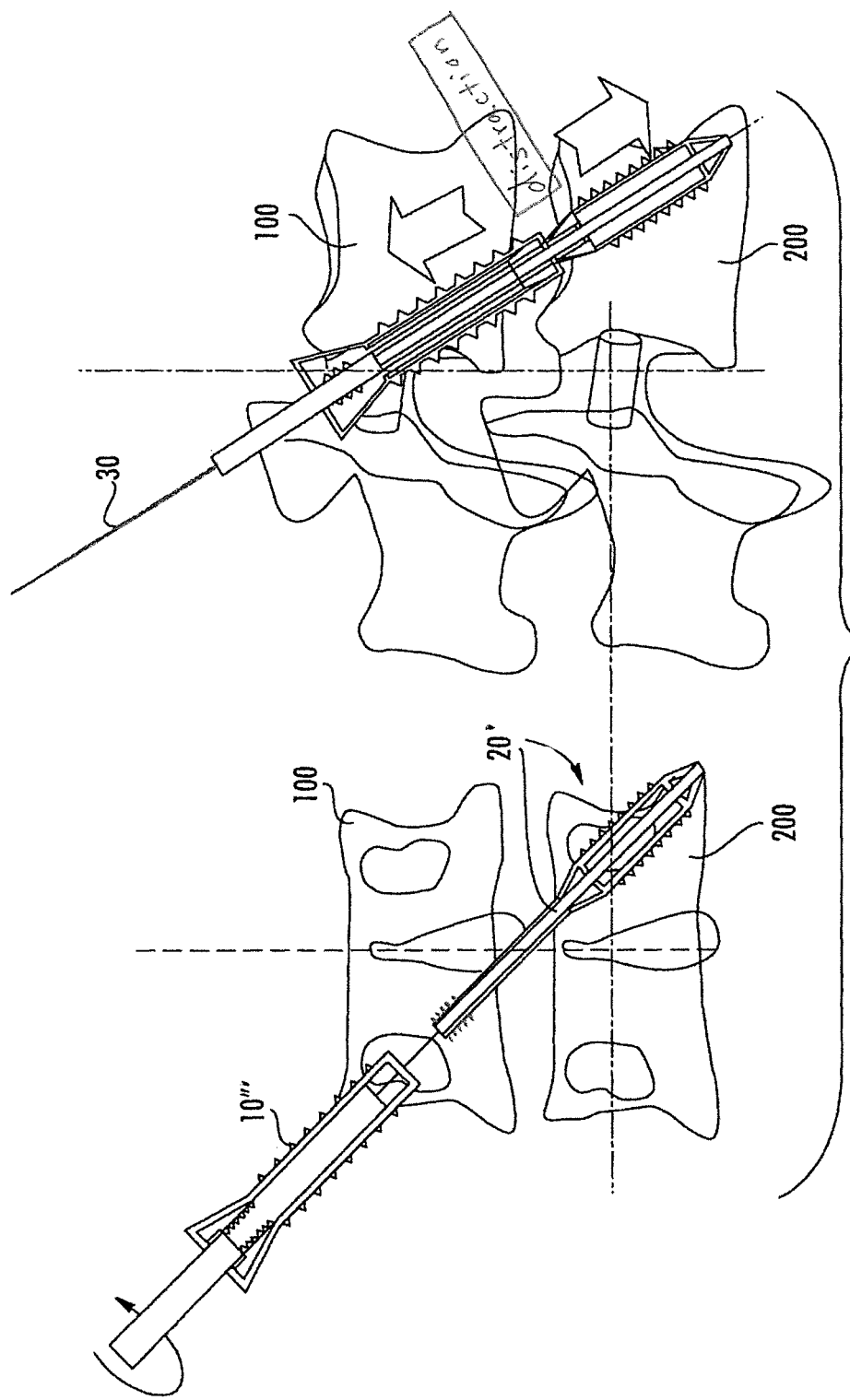
Figure 60:
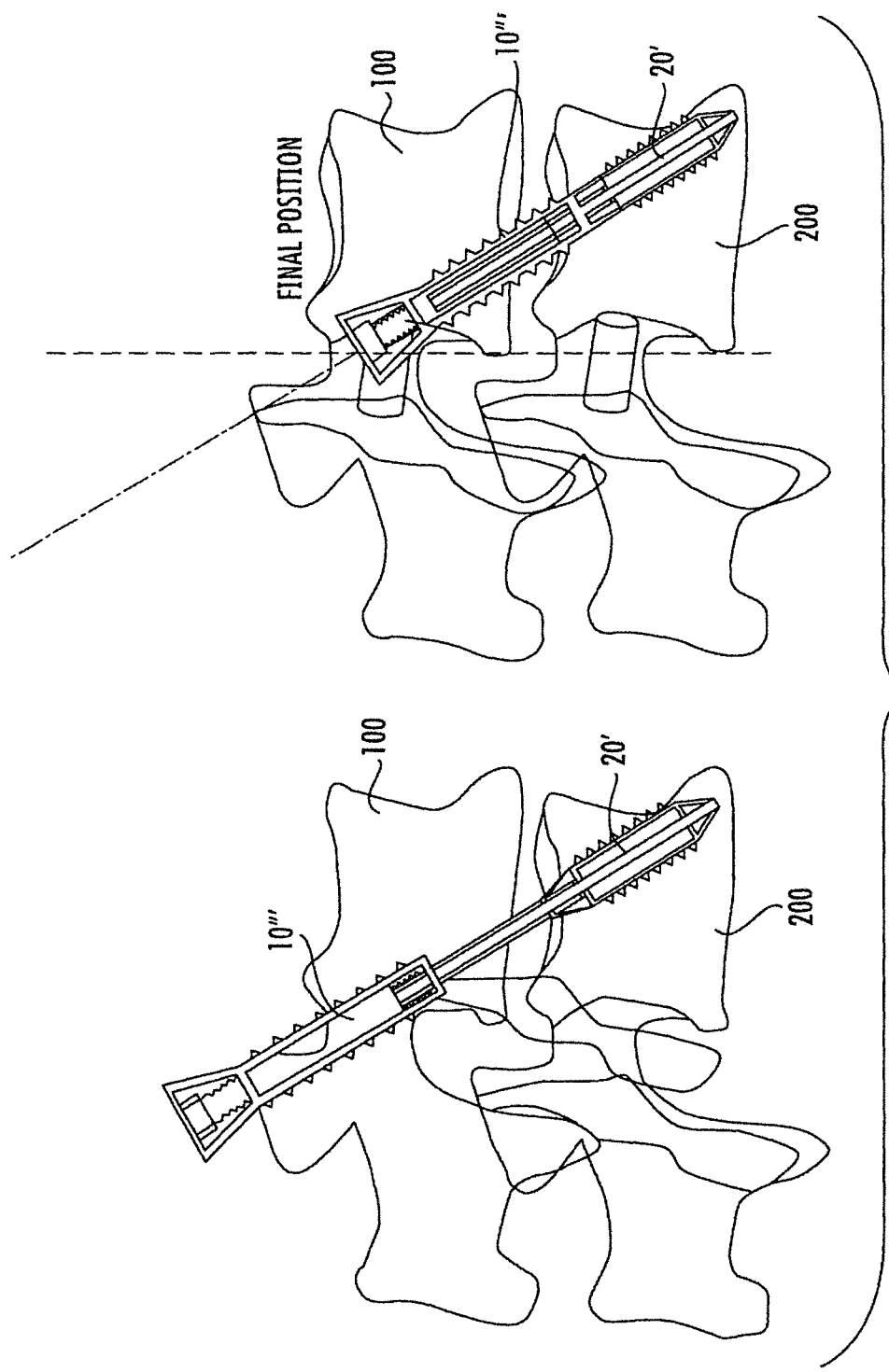
FIG. 60 shows the screw according to FIG. 57 onto which the casing according to FIG. 57 is screwed on with another position of the casing.
Figure 61:
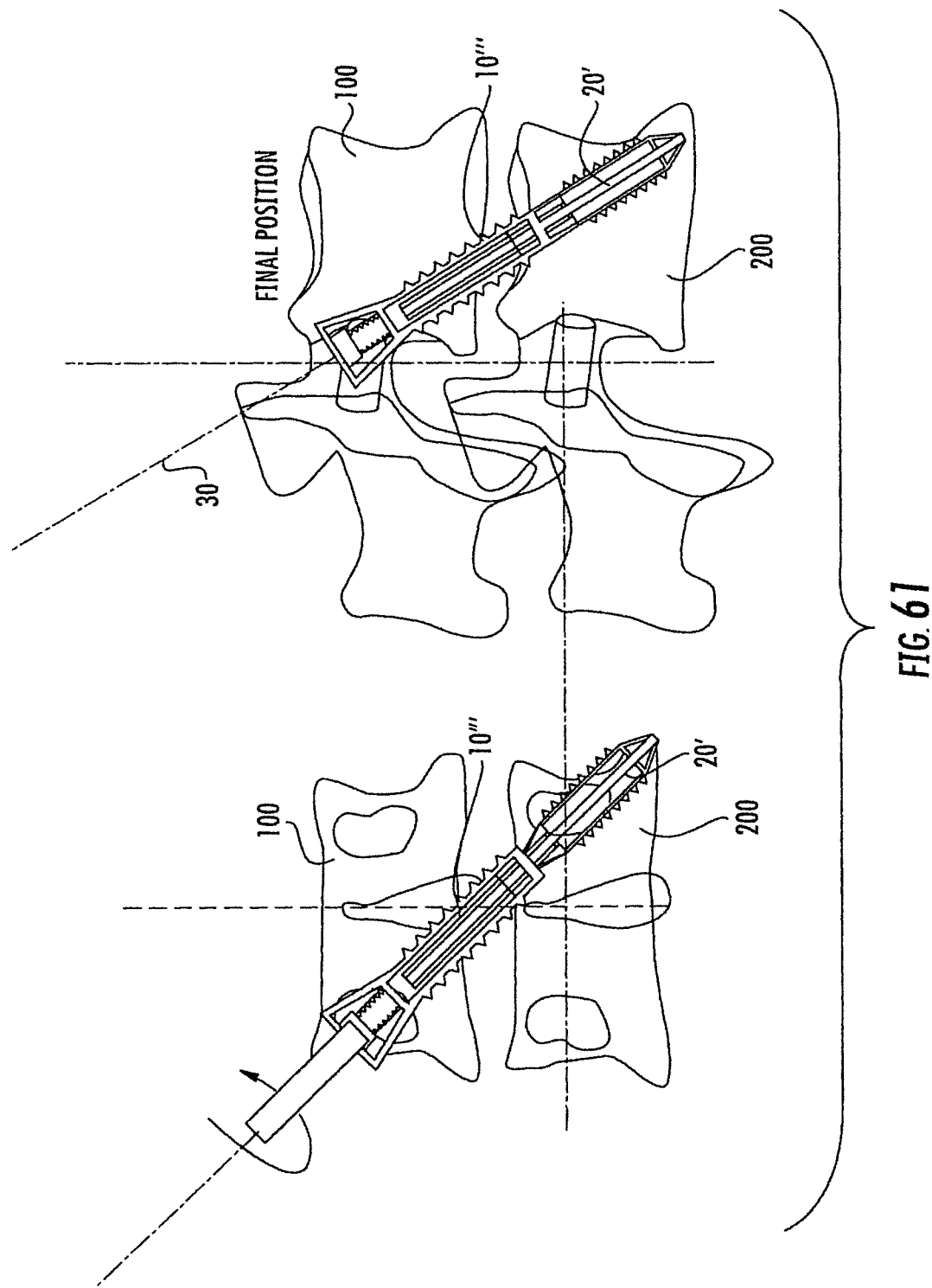
FIG. 61 shows the screw according to FIG. 57 onto which the casing according to FIG. 22 is screwed on with another position of the casing.
Figure 62:
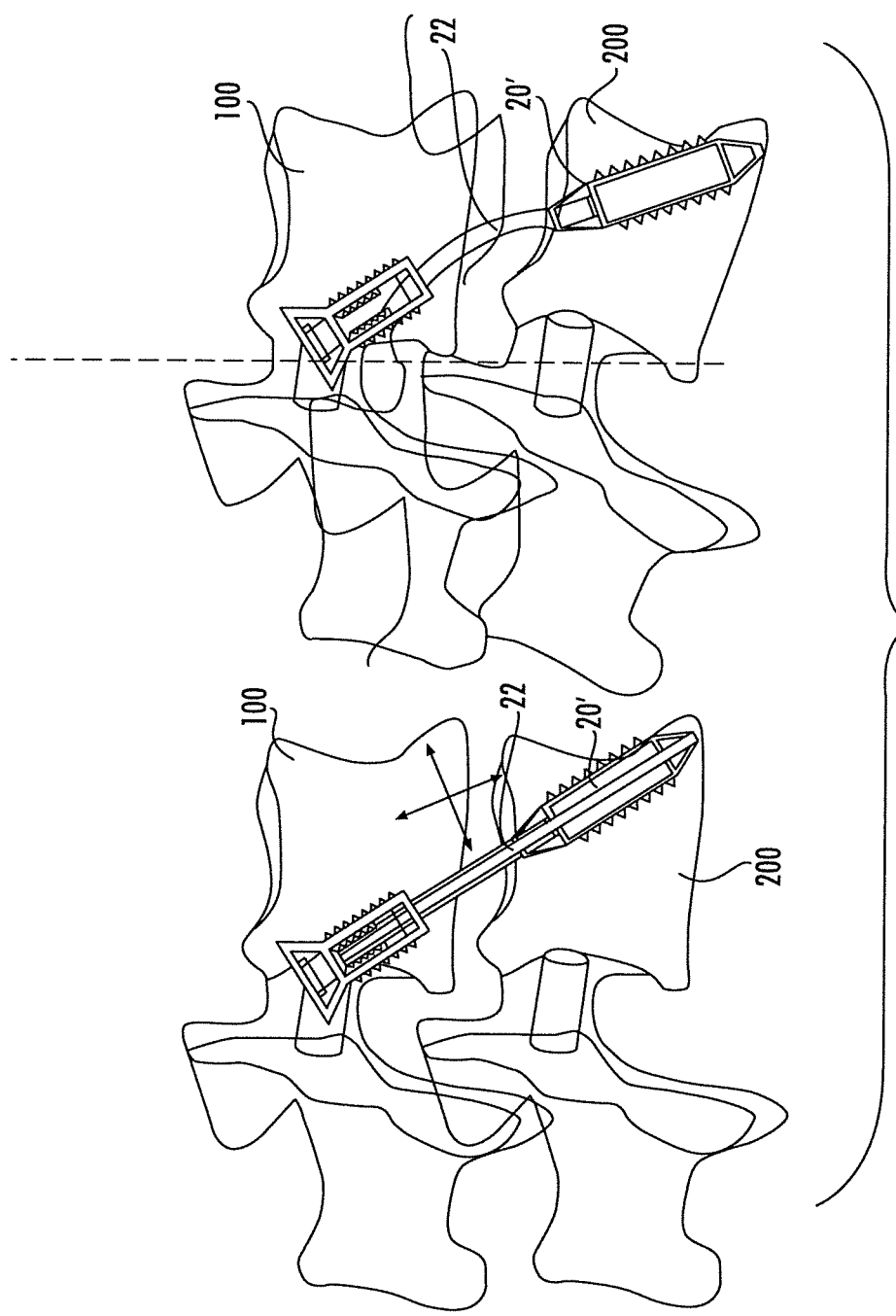
FIG. 62 shows the screw according to FIG. 57 onto which the casing according to FIG. 57 is screwed on with another position of the casing.

FIGS. 55 to 57 show another exemplary embodiment of a casing 10''' with another exemplary embodiment of a screw 20'. FIGS. 58 to 62 show how casing 10''' and screw 20' are introduced into two adjacent vertebral bodies 100, 200.

FIGS. 55 to 57 show different views of a first exemplary embodiment of a casing 10''' with the front section 11 and a following rear area 13. Front area 11 carries an outer threading 14. An inner threading 16 for the first pitch is arranged in rear section 13. Rear section 13 can be conically designed for better stabilization.

Screw 20' has a front section 21 and a following central area 22 followed by rear section 23. A first outer threading 24 is arranged in front section 21 of screw 20 whereas a second outer threading 25 is arranged in rear section 23. The first outer threading 24 has a third pitch, whereas second outer threading 25 has a fourth pitch. However, the fourth pitch of the second outer threading 25 corresponds in particular to the first pitch of the first inner threading 16 of casing 10. The third pitch and the fourth pitch can be differently selected.

As can be recognized in FIGS. 58 to 62, at first screw 20' is introduced, in particular along a guide wire 30, into vertebral body 100, 200, whereby screw 20' is screwed through upper vertebral body 100 until into lower vertebral body 200, whereby screw 20' passes through intervertebral space 53. The central area 12 comes to lie in intervertebral space 53 (cf. FIGS. 58 and 59). Subsequently, casing 10''' is rotated onto screw 20' (cf. FIGS. 59 to 62), during which second outer threading 25 of screw 20' engages into inner threading 16 of casing 10'''. Casing 10''' can, in particular, be screwed in so far that a stop 26 of screw 20' is drawn against the distal edge of casing 10''' and vertebral bodies 100, 200 are subsequently distracted (cf. FIGS. 59, 60 and 61). Alternatively, casing 10''' can also be screwed on only so far that it remains in superior vertebral body 100 and only the central section 22 of screw 20' passes through intervertebral space 53 (cf. FIG. 62).

In one embodiment central section 22 of screw 20' is elastically constructed. If casing 10''' is screwed on only so far that it remains in superior vertebral body 100, and only the central section 22 of screw 20' passes through intervertebral space 53, there is the possibility of tilting vertebral bodies 100, 200 toward one another and moving them relative to one another so that an intervertebral disk can be simulated in this manner (cf. FIG. 62).

A good stabilization of the two vertebral bodies 100, 200 relative to one another can be achieved in particular given the formation of bone screw 20 as compression screw, especially if an intervertebral disk prosthesis is additionally introduced into intervertebral space 250.

Embodiments of an intervertebral disk prosthesis are described in the following.

Figure 22:
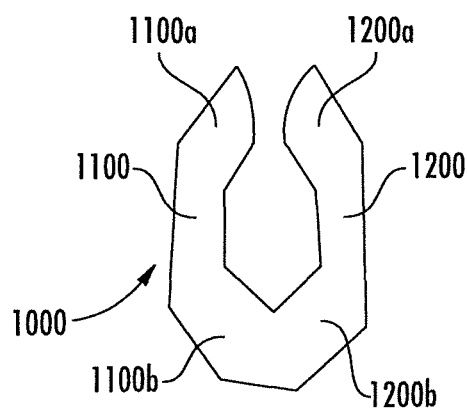
FIG. 22 shows a schematic view of a first exemplary embodiment of an intervertebral disk prosthesis.

FIG. 22 shows a top view onto first exemplary embodiment of an intervertebral disk prosthesis 1000 with a first shank 1100 that has a first end 1100a and a second end 1100b and has a second shank 1200 that has a first end 1200a and a second end 1200b. The two shanks 1100, 1200 are connected to each other in one piece on their second ends 1100b, 1200b. The free ends 1100a, 1200a are bent toward one another so that an almost closed ring with a slot results. Intervertebral disk prosthesis 1000 is manufactured from an elastic material, which makes it possible that the two shanks 1100, 1200 can be pivoted toward one another. The pivoting of the two shanks 1100, 1200 toward one another takes place in the plane in which the U-shaped element lies. In the present instance this is in particular the paper plane.

Figure 23:
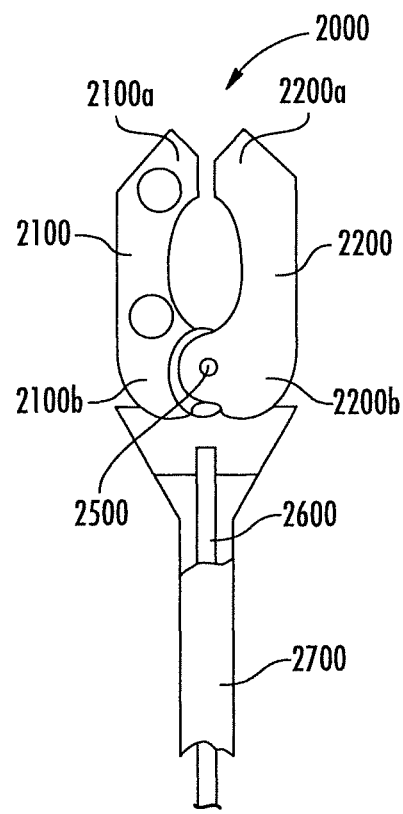
FIG. 23 shows a schematic view of a second exemplary embodiment of an intervertebral disk prosthesis.

FIG. 23 shows a top view onto a second exemplary embodiment of an intervertebral disk prosthesis 2000 with a first shank 2100 that has a first end 2100a and a second end 2100b and with a second shank 2200 that has a first end 2200a and a second end 2200b. The first ends 2100a, 2200a are designed as free ends whereas the two shanks 2100, 2200 are connected to each other on their second ends 2100b, 2200b. This connection takes place by a bolt 2500. In the exemplary embodiment according to FIG. 23, the two shanks 2100, 2200 are directly supported against one another in a rotatable manner by a single bolt 2500. Alternatively, it is also possible to arrange each of the two shanks 2100, 2200 pivotably on a connection element by a separate bolt. Bolt 2500 runs substantially vertically to the plane of substantially U-shaped intervertebral disk prosthesis 2000, in particular vertically to the paper plane in the drawing. As a result, the two shanks 2100, 2200 are pivotably supported against one another in the plane of U-shaped intervertebral disk prosthesis 2000, i.e., in the paper plane. A pivoting open of the two shanks 2100, 2200 toward one another can take place, for example, in that a spreading-open element 2600 of a holder 2700 is thrust between the two shanks 2100, 2200 and that the two shanks 2100, 2200 are formed with such a compulsory curve on their second ends 2100h, 2200b that they escape from spreading-open element 2600 and are pivoted relatively toward one another.

Figure 24:
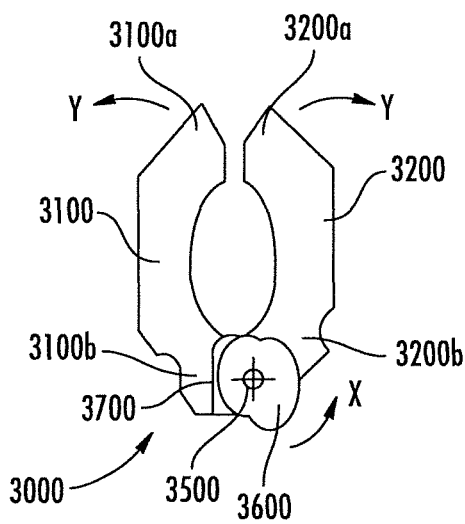
FIG. 24 shows a schematic view of a third exemplary embodiment of an intervertebral disk prosthesis.

FIG. 24 shows a top view onto a third exemplary embodiment of a intervertebral disk prosthesis 3000 with a first shank 3100 that has a first end 3100a and a second end 3100b and with a second shank 3200 that has a first end 3200a and a second end 3200b. The two shanks 3100, 3200 are arranged pivotably supported against one another viable 3500 similar to the second exemplary embodiment of the intervertebral disk prosthesis 2000, whereby bolt 3500 runs substantially vertically to the plane of the substantially U-shaped intervertebral disk prosthesis 3000, i.e., substantially vertically to the paper plane in the present representation. A pivoting open of the two shanks 3100, 3200, relative to one another, takes place in the third exemplary embodiment by means of a lever element 3600 arranged on intervertebral disk prosthesis 3000. Lever element 3600 is also supported in such a manner that it can pivot about bolt 3500 and is constructed, for example, as an eccentric element. During the pivoting of lever element 3600 in pivoting direction X, lever element 3600 attacks, for example, a compulsory curve 3700 arranged on second end 3100b of first shank 3100 in order to pivot the two shanks 3100, 3200 apart for one another in pivoting direction Y. A corresponding compulsory curve can also be arranged on free end 3200b of second shank 3200 which curve brings about a pivoting apart of the two shanks 3100, 3200 during the pivoting of lever element 3600 about bolt 3500.

Figure 25:
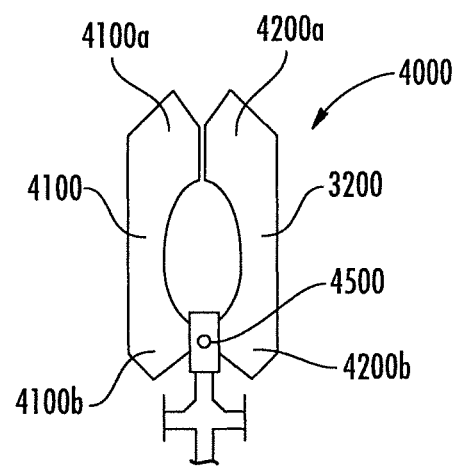
FIG. 25 shows a schematic view of a fourth exemplary embodiment of an intervertebral disk prosthesis.

FIG. 25 shows a top view onto a fourth exemplary embodiment of an intervertebral disk prosthesis 4000 with a first shank 4100 that has a first end 4100a and a second end 4100b and with a second shank 4200 that has a first end 4200a and a second end 4200b, whereby the two shanks 4100, 4200 are connected to one another by a cylindrical articulation 4500. An actuation element 4600 can be inserted into cylindrical articulation 4500 in order to pivot the two shanks 4100, 4200 toward one another.

Figure 26:
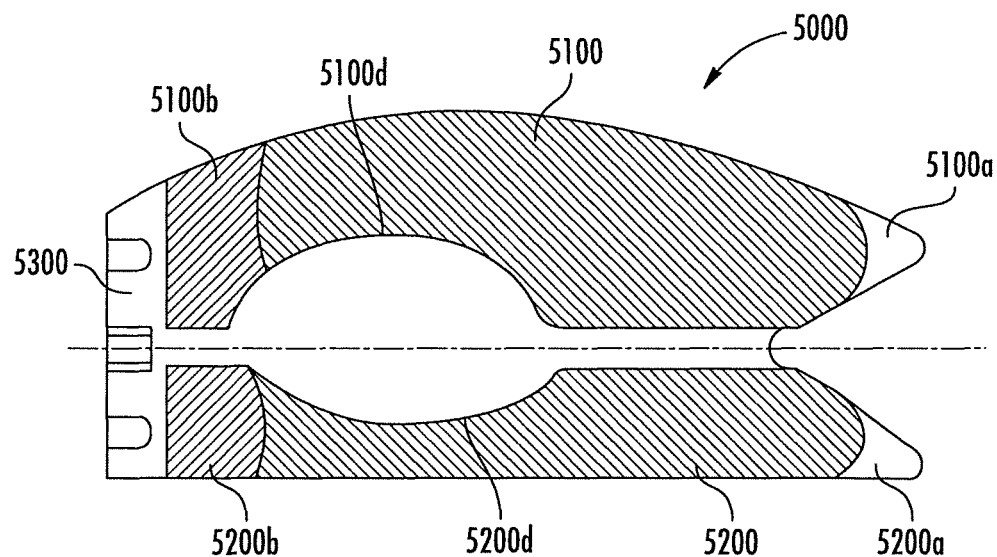
FIG. 26 shows a schematic view of a fifth exemplary embodiment of an intervertebral disk prosthesis.
Figure 27:
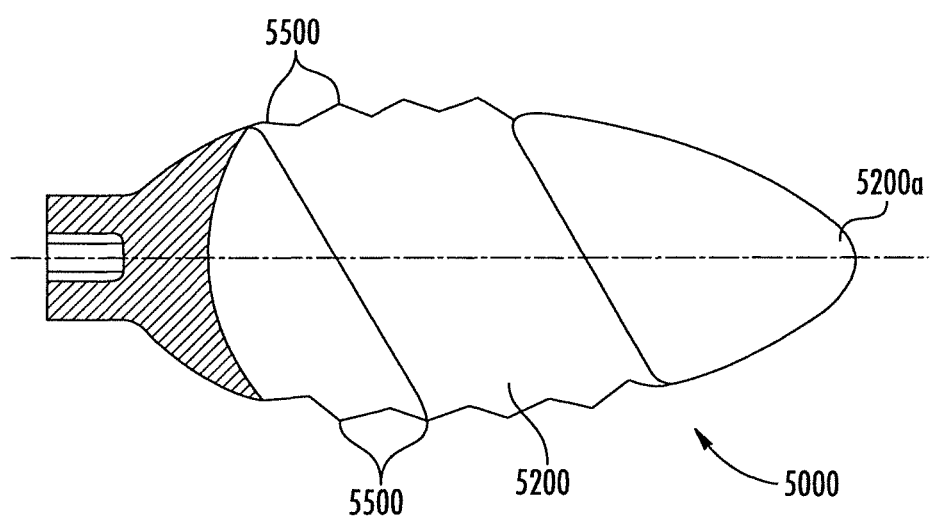
FIG. 27 shows a side view of the intervertebral disk prosthesis according to FIG. 26.
Figure 28:
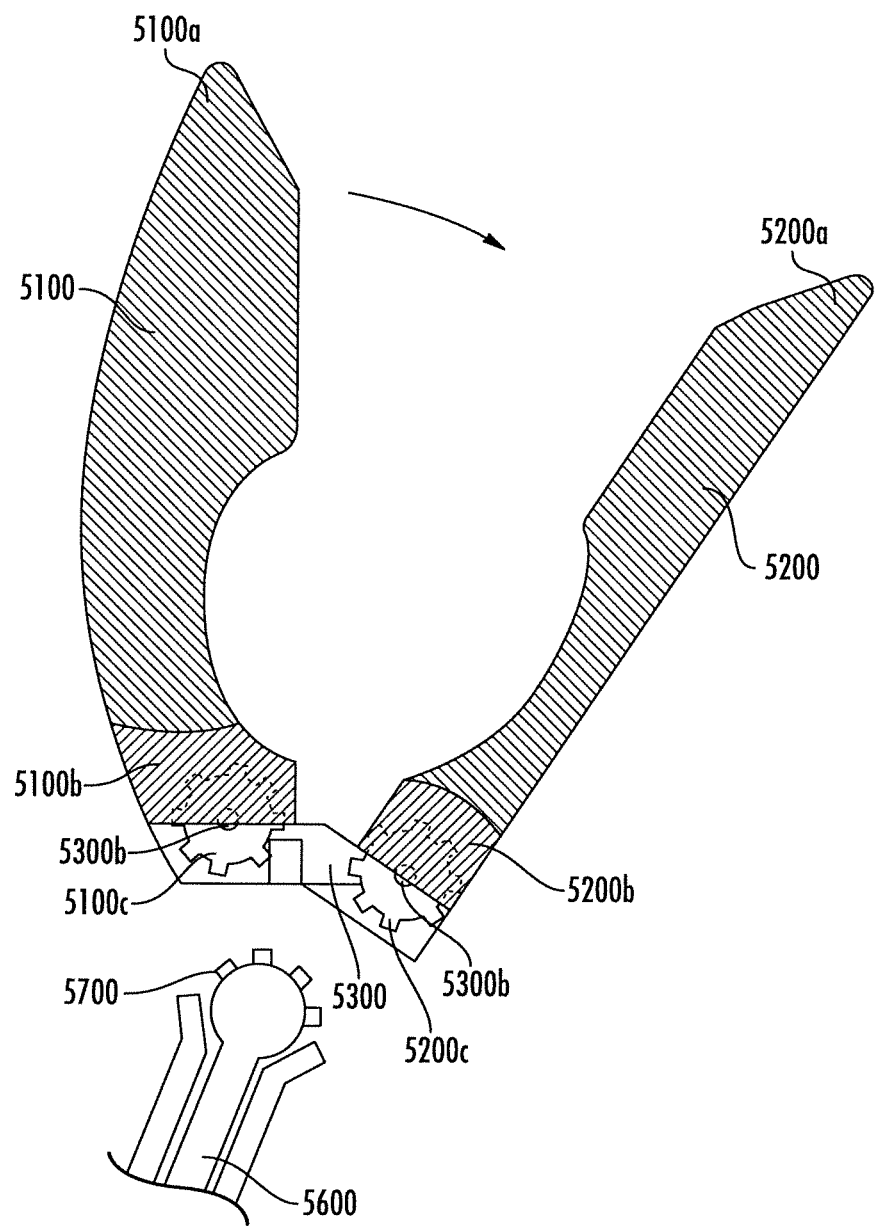
FIG. 28 shows the intervertebral disk prosthesis according to FIG. 26 in a pivoted-open state.
Figure 29:
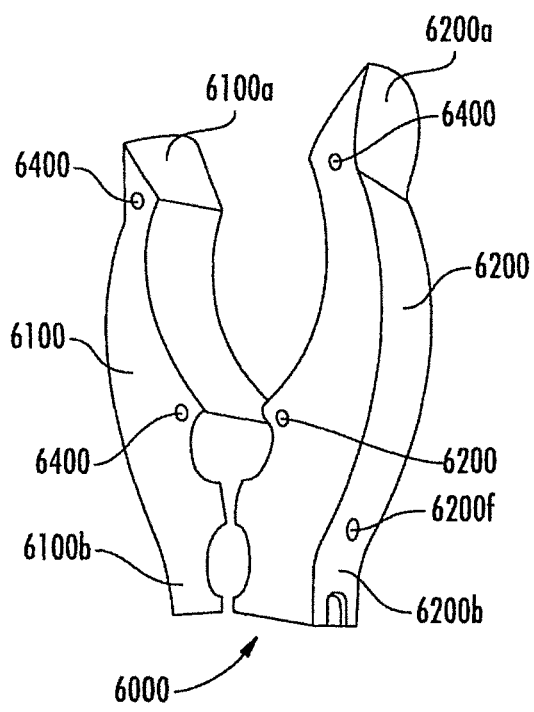
FIG. 29 shows a schematic perspective view of a sixth exemplary embodiment of an intervertebral disk prosthesis.

FIGS. 26 to 28 show a fifth exemplary embodiment of an intervertebral disk prosthesis 5000. Intervertebral disk prosthesis 5000 has a first shank 5100 and a second shank 5200, which first shank 5100 has a first end 5100a and a second end 5100b whereas the second shank 5200 has a first end 5200a and a second end 5200b. The two shanks 5100, 5200 are connected to one another on their second ends 5100b, 5200b by a connecting element 5300. The first shank 5100 is pivotably supported by a bolt 5300a on connecting element 5300 whereas second shank 5200 is pivotably supported by a bolt 5200b on connecting element 5300. Furthermore, the two ends 5100b, 5200b of shanks 5100, 5200 are equipped with a geared section 5100c, 5200c, which geared sections 5100c, 5200c are arranged in particular concentrically around the particular bolts 5300a, 500b. During the introduction of intervertebral disk prosthesis 5000 into an intervertebral space, the two shanks 5100, 5200 lie substantially parallel (compare FIG. 26). After the introduction of intervertebral disk prosthesis 5000 into the intervertebral space, a spreading-open element 5600 is introduced between the two second ends 5100b, 5200b of shanks 5100, 5200. Spreading-open element 5600 has a geared section 5700 corresponding to geared sections 5100c, 5200c of shanks 5100, 5200 by means of which geared section 5700 the two shanks 5100, 5200 are spread further apart the further spreading-open element 5600 is introduced between the two shanks 5100, 5200.

In order to be able to visually follow the introduction and positioning of intervertebral disk prosthesis 5000 in the intervertebral space, in particular the first ends 5100a, 5200a are provided with an x-ray contrast material, for example, coated with tantalum. Another x-ray contrast marker is preferably arranged in the third place. Preferably, at least three x-ray contrast markers are arranged on intervertebral disk prosthesis 5000 that also do not necessarily have to be arranged on the free ends 5100a, 5200a of shanks 5100, 5200. Of course, the x-ray contrast markers can also be used with all other intervertebral disk prostheses described in the present Application.

Shanks 5100, 5200 each have a recess 5100d, 5200d on the lateral surfaces facing each other. In particular a bone screw that stabilizes two adjacent vertebral bodies against one another can be run through this area.

As can be recognized in the lateral view according to FIG. 27 the upper and lower sides of shanks 5100, 5200 can be designed curved in order to adapt to the anatomic conditions. In particular, the upper and/or lower side(s) of intervertebral disk prosthesis 5000 can have teeth 5500 in order to improve an anchoring of intervertebral disk prosthesis 5000 in the adjacent vertebral body.

The first shank 5100 has in the present instance a larger side than shank 5200 (compare FIGS. 26 and 28) in order to achieve a uniform stabilization of the two adjacent vertebral bodies against one another for the case that the bone screw connecting the two adjacent vertebrae to one another is not centrally guided through the intervertebral space.

FIGS. 28 to 34 show different views of a sixth exemplary embodiment of an intervertebral disk prosthesis 6000 whereas FIGS. 35 to 44 show in what manner intervertebral disk prosthesis 6000 can be introduced into the intervertebral space.

Figure 30:
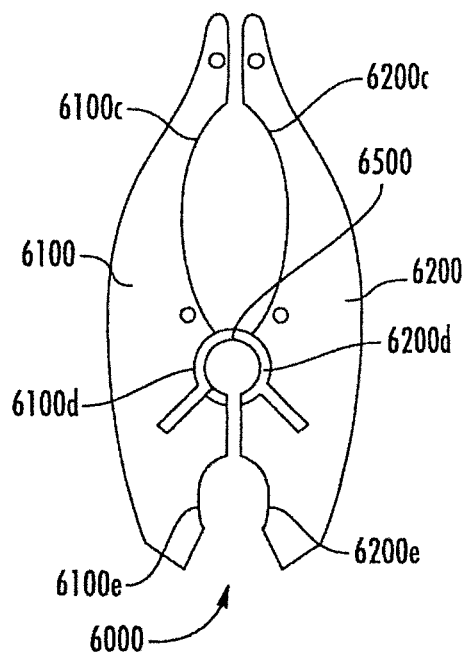
FIG. 30 shows a top view onto the intervertebral disk prosthesis according to FIG. 29 in the folded-together state.
Figure 31:
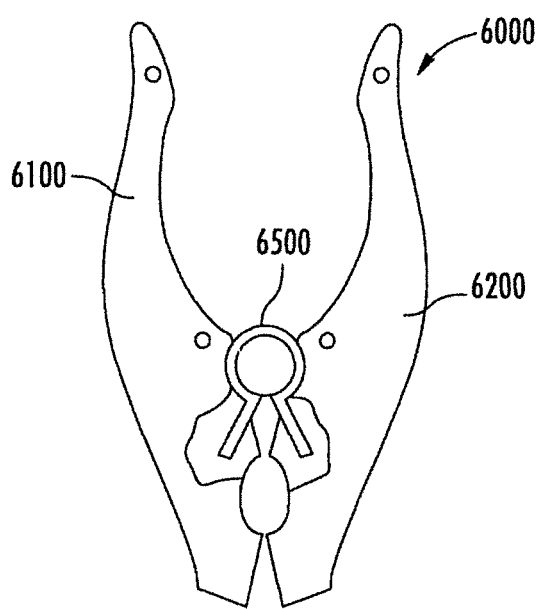
FIG. 31 shows the intervertebral disk prosthesis according to FIG. 29 in a pivoted-open state.
Figure 32:
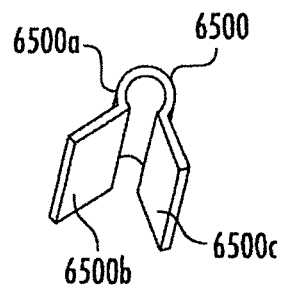
FIG. 32 shows a perspective view of the spring element of the intervertebral disk prosthesis according to FIG. 30.
Figure 34:
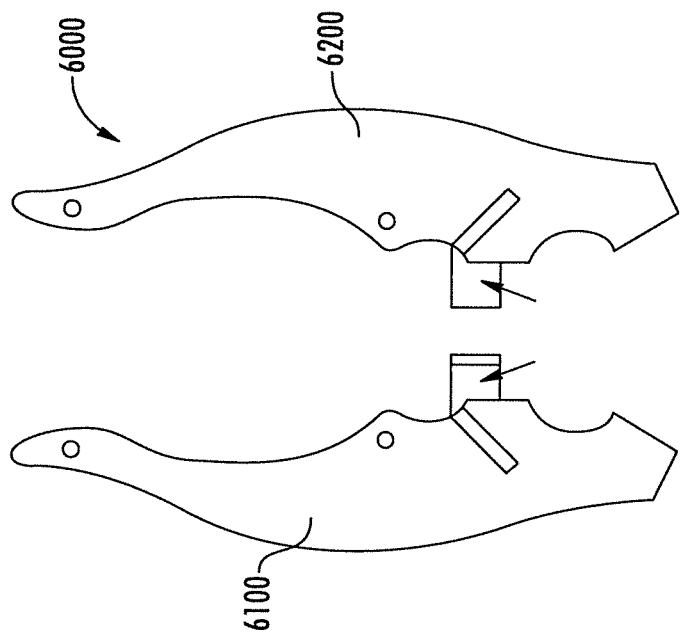
FIG. 34 shows a top view onto the disassembled intervertebral disk prosthesis according to FIG. 29.
Figure 33:
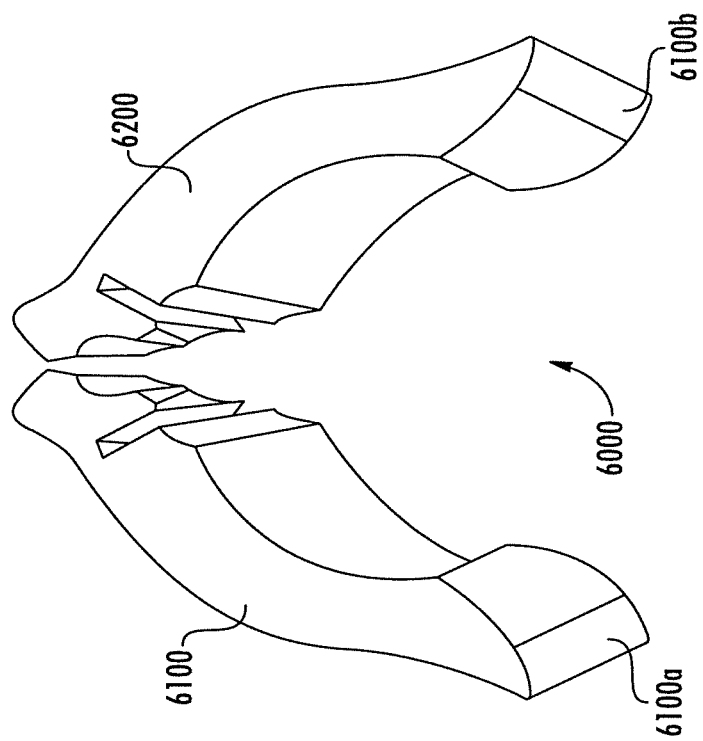
FIG. 33 shows a perspective view of the intervertebral disk prosthesis according to FIG. 29 in a spread-open state.

Intervertebral disk prosthesis 600 has a first shank 6100 and a second shank 6200 which first shank 6100 has a first end 6100a and a second end 6100b, whereas the second shank 6200 has a first end 6200a and a second end 6200b. The two shanks 6100, 6200 have a second recess 6100d, 6200d on the side surface facing the other one between the first end 6100a, 6200a and between the second end 6100b, 6200b. The two shanks 6100, 6200 are connected to one another by a spring element 6500 (cf. FIG. 32) that engages, as described in the following, into the second recess 6100d, 6200d of shanks 6100, 6200. Spring element 6500 has a substantially cylindrical section 6500a that is slotted over its entire length and on which, starting from the slot, two anchoring wings 6500b, 6500c are arranged. Anchoring wings 6500b, 6500c can therefore pivot substantially about the longitudinal axis of cylindrical section 6500a of spring element 6500. One anchoring ring 6500b, 6500c at a time engages into one of the two recesses 6100d, 6200d of shanks 6100, 6200 (compare in particular FIGS. 30 and 31). Here, FIG. 31 shows the state of spring element 6500 without outside action of force. Thus, spring element 6500 is relaxed when the two shanks 6100, 6200 are spread open relative to one another. On the other hand, FIG. 30 shows spring element 6500 in the loaded state. The two shanks 6100, 6200 are moved into a closed position counter to the force of spring element 6500 in which position they run in particular substantially parallel to one another.

A first recess 6100c, 6200c is arranged between the second recess 6100d, 6200d and the first ends 6100a, 6200a of shanks 6100, 6200 on the side surfaces of shanks 6100, 6200 facing one another, through which recesses in particular a bone screw connecting the two adjacent vertebral bodies can be run as a stabilizing element, for example, bone screw 20 previously described using FIG. 4.

A third recess 6100e, 6200e is arranged between second recess 6100d, 6200d and the second ends 6100b, 6200b of shanks 6100, 6200 on the side surfaces of shanks 6100, 6200 facing one another into which third recess an insertion instrument 6600 can engage as described in the following using FIGS. 14 and 15.

Several x-ray contrast markers are arranged on shanks 6100, 6200, in particular in the area of first ends 6100a, 6200a of shanks 6100, 6200 and in the area between second recess 6100d, 6200d and first recess 6100c, 6200c in order to be able to follow visually the insertion of intervertebral disk prosthesis 6000.

Figure 35:
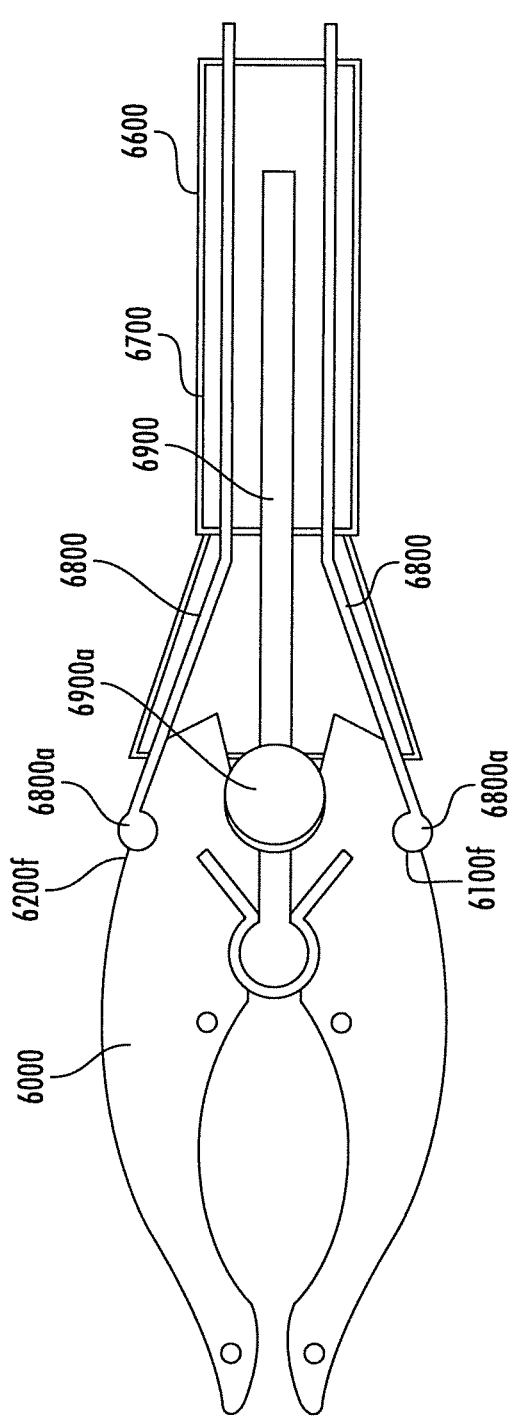
FIG. 35 shows the intervertebral disk prosthesis according to FIG. 29 in a folded-together state that is inserted into a holder.
Figure 36:
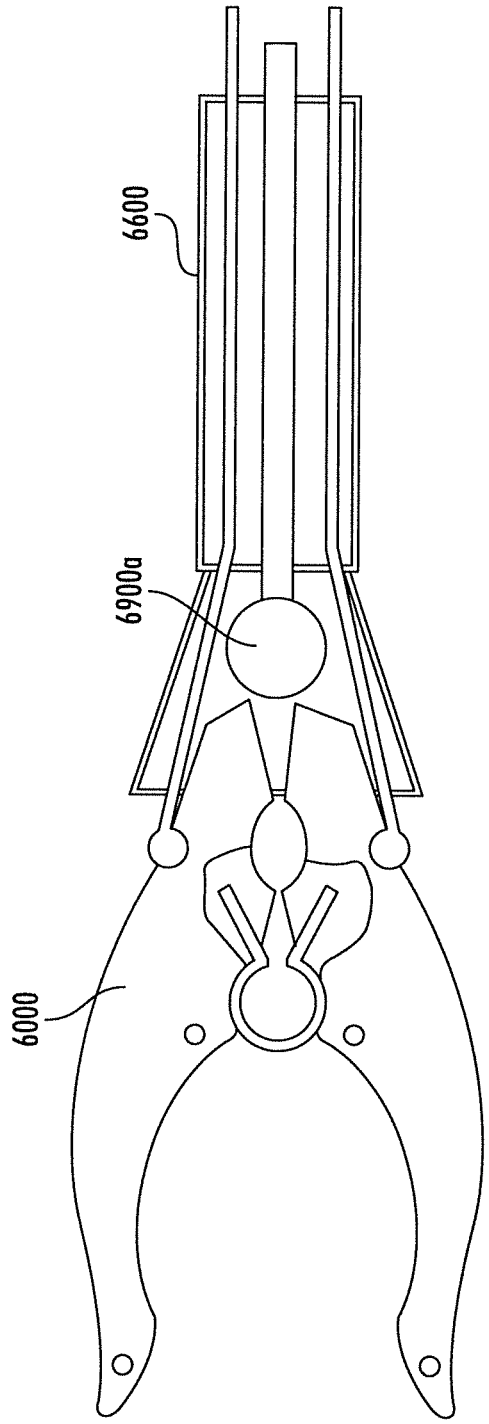
FIG. 36 shows the intervertebral disk prosthesis according to FIG. 29 in a spread-open state that is inserted into a holder.
Figure 37:
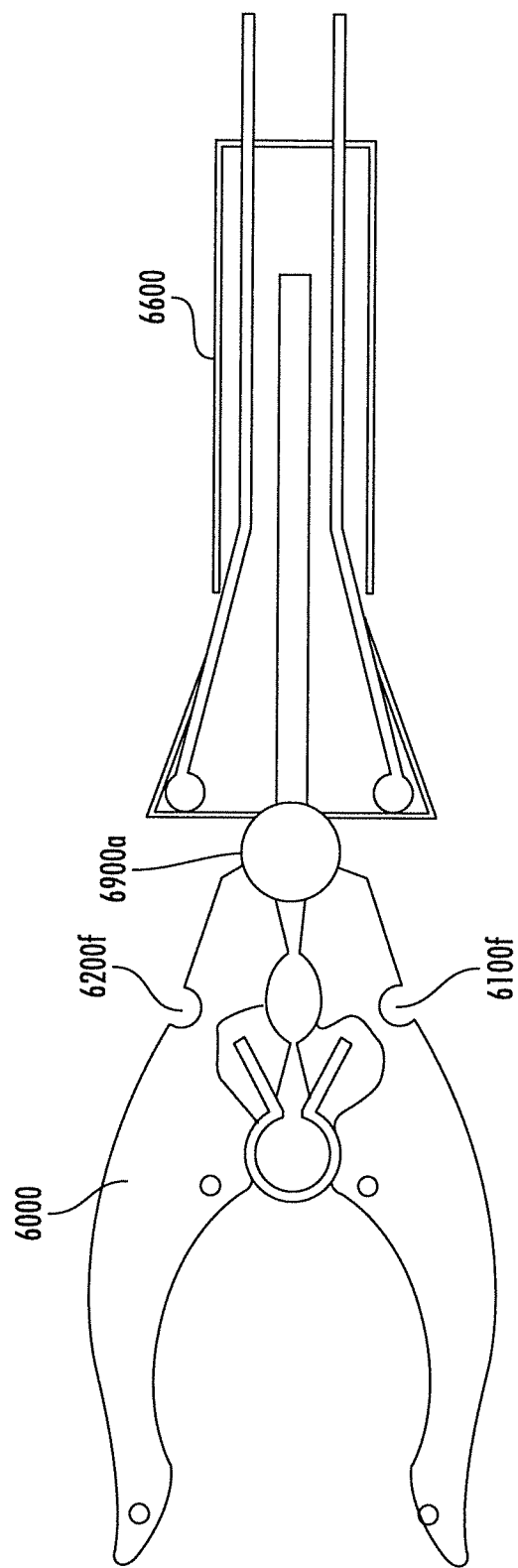
FIG. 37 shows the intervertebral disk prosthesis according to FIG. 29 with the holder separated from it.

FIGS. 35 to 37 show insertion instrument 6600 in detail, which has a casing 6700 in which two holding elements 6800 and a spreading-open element 6900 are arranged in an axially shiftable manner. Holding elements 6800 have gripping elements 6800a on their distal end that are constructed in the present instance as spheres or cylinders that engage into fourth recesses 6100f, 6200f substantially positively and are arranged on the outer side surfaces of shanks 6100, 6200 which side surfaces face away from the particular other shank 6100, 6200. Gripping elements 68001 can lock in recesses 6100f, 6200f or be held in them in a clamping manner or only rest in them in a substantially positive manner. Spreading-open element 6900 has an element 6900a on its distal end which element can also be constructed as a spherical or cylindrical element and which engages into third recess 6100e, 6200e of intervertebral disk prosthesis 6000.

Figure 38:
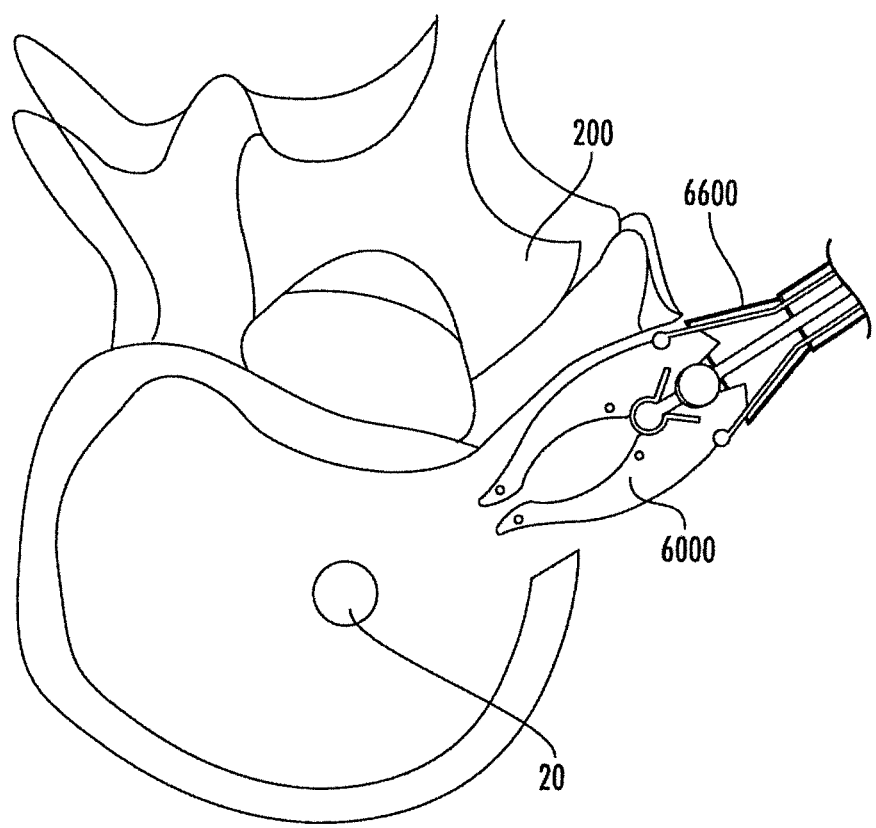
FIG. 38 shows a view of the introduction of the intervertebral disk prosthesis according to FIG. 29 into an intervertebral space.
Figure 39:
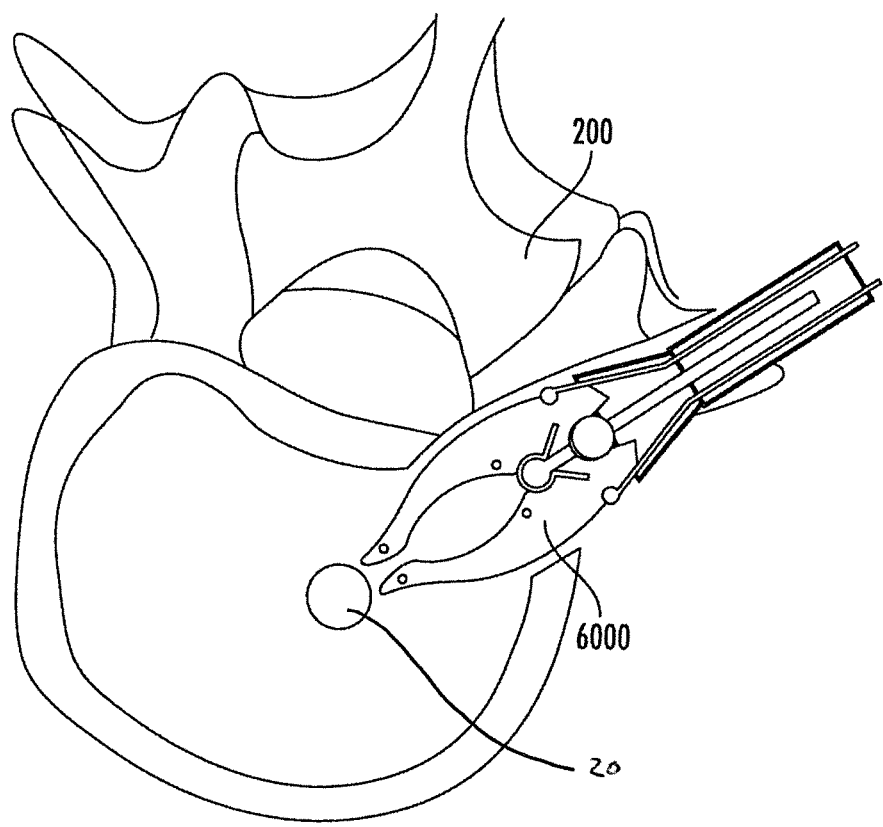
FIG. 39 shows another view of the insertion of the intervertebral disk prosthesis according to FIG. 29 into an intervertebral space.
Figure 40:
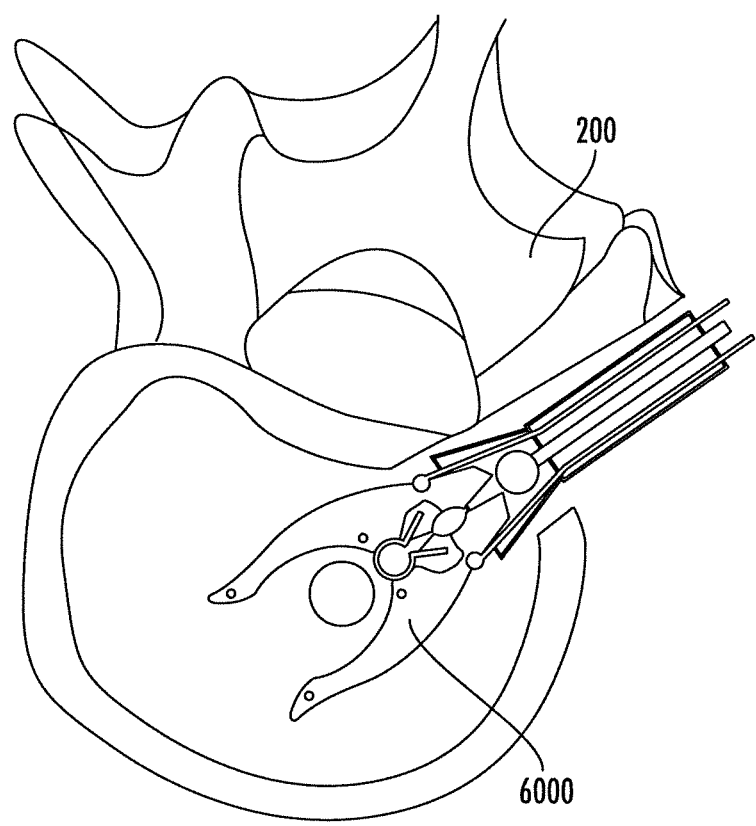
FIG. 40 shows another view of the insertion of the intervertebral disk prosthesis according to FIG. 29 into an intervertebral space.
Figure 41:
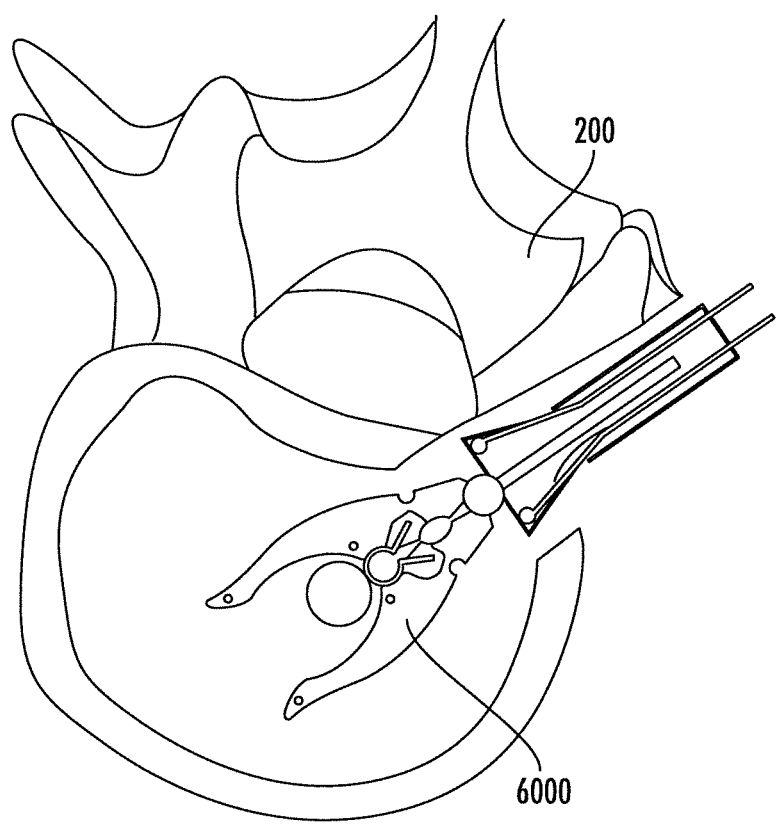
FIG. 41 shows another view of the insertion of the intervertebral disk prosthesis according to FIG. 29 into an intervertebral space.
Figure 42:
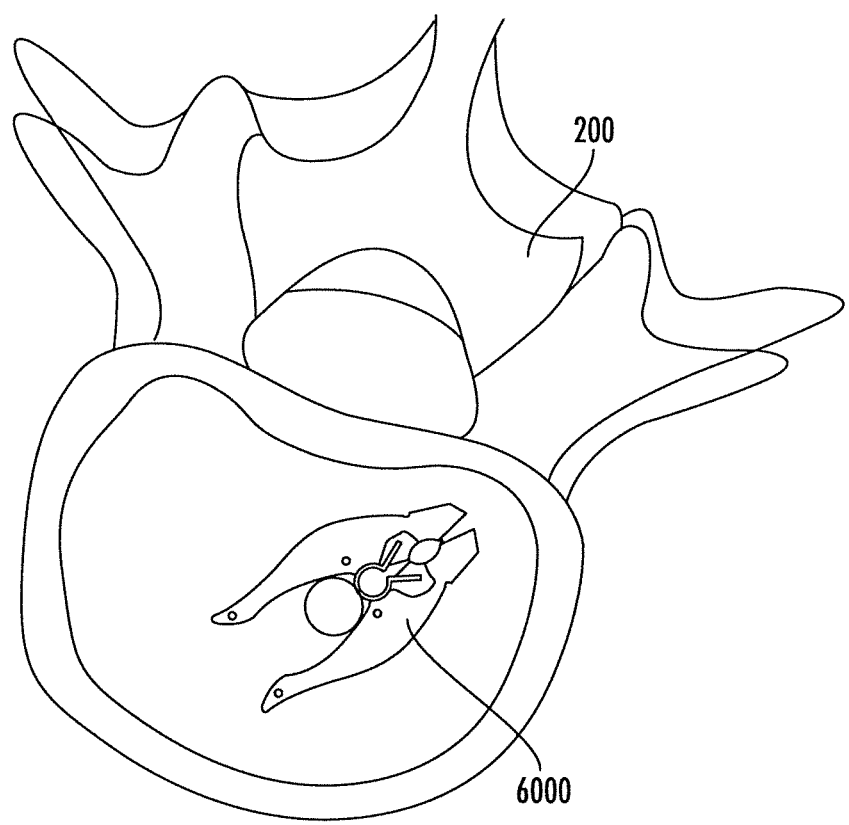
FIG. 42 shows another view of the insertion of the intervertebral disk prosthesis according to FIG. 29 into an intervertebral space.
Figure 43:
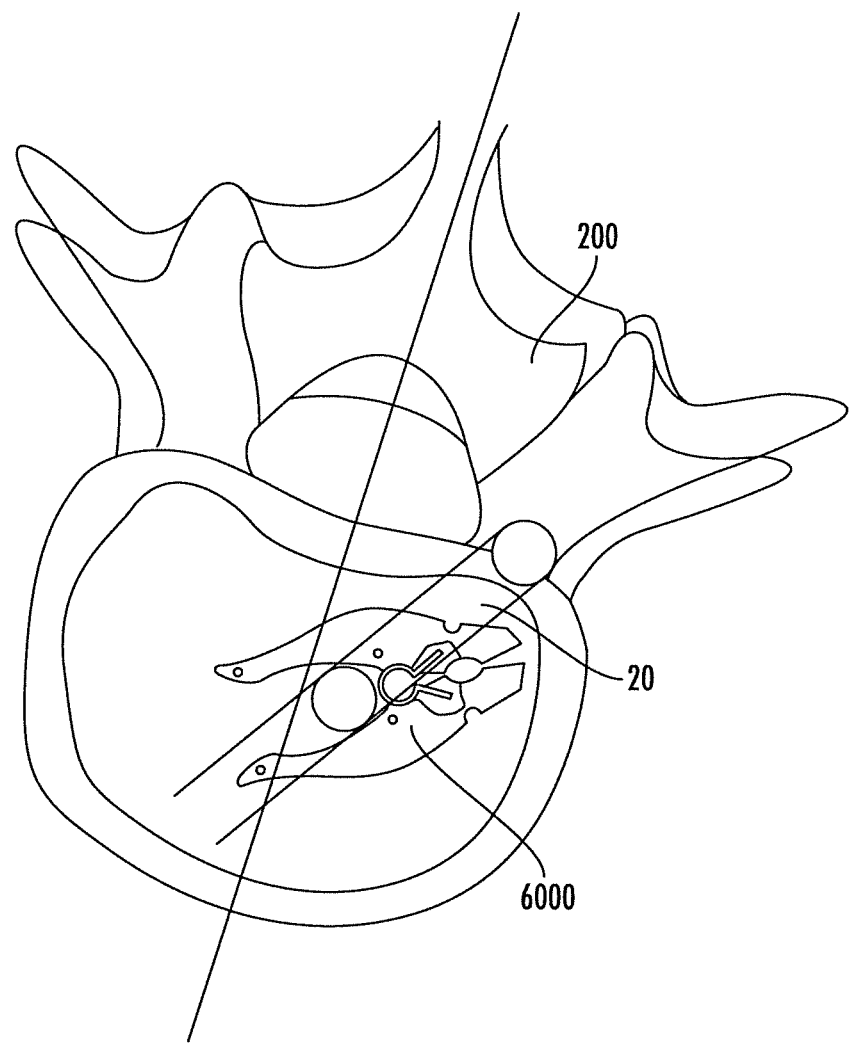
FIG. 43 shows the intervertebral disk prosthesis according to FIG. 29 in the state inserted into the intervertebral space with a schematic perspective view of a bone screw.
Figure 44:
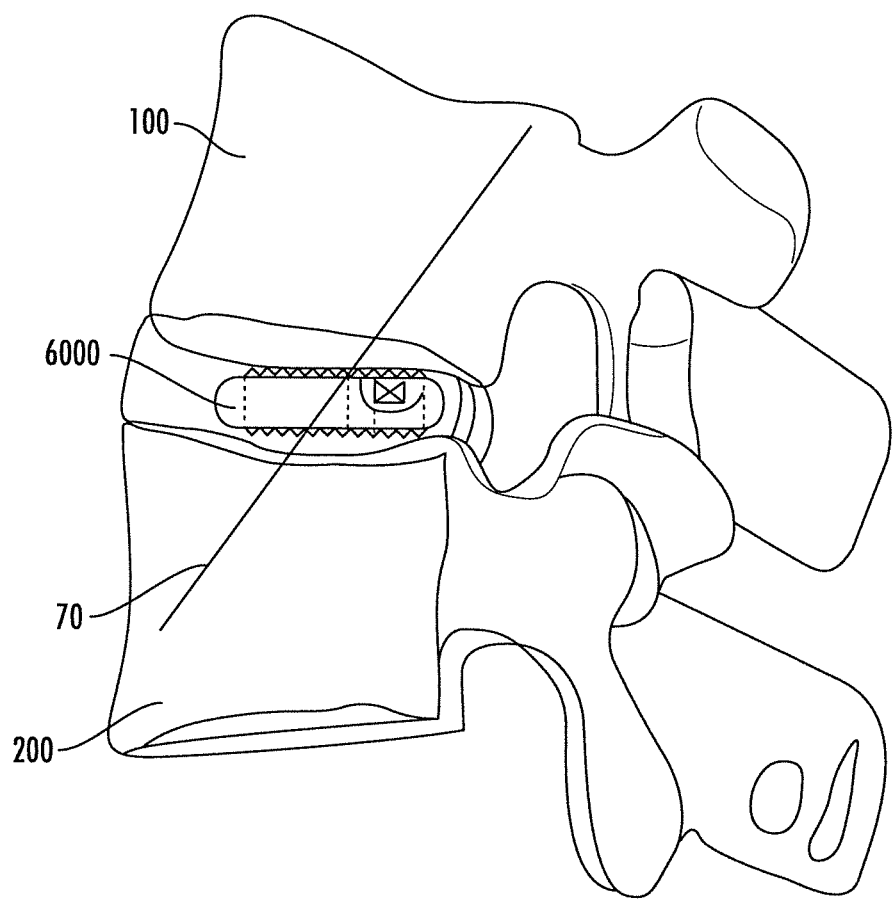
FIG. 44 shows a side view of the intervertebral disk prosthesis in the state inserted into the intervertebral space between two adjacent vertebrae with a schematic view of the bone screw.

As FIG. 35 shows, spring element 6500 is widened against the spring force by the insertion of element 6900a of spreading-open element 6900 into the third recesses 6100e, 6200e and the two shanks 6100, 6200 are moved into a closed position. At the same time, gripping elements 6800a of holding elements 6800 engage into fourth recesses 6100f, 6200f of shanks 6100, 6200 in order to hold intervertebral disk prosthesis 6000. In this position, intervertebral disk prosthesis 6000 can be introduced between two adjacent vertebral bodies 100, 200, as shown in FIGS. 38 and 39. In order to spread the intervertebral disk prosthesis open, spreading-open element 6900 is withdrawn axially in casing 6700 of insertion instrument 6600 so that shanks 6100, 6200 are spread open relative to one another by the force of spring element 6500 (compare FIG. 36 and FIG. 40). Intervertebral disk prosthesis 6000 can subsequently be shifted into the intervertebral space to the desired position by holding elements 6800 (compare FIG. 40). Subsequently, even holding elements 6800 can be separated from intervertebral disk prosthesis 6000 by axially withdrawing holding elements 6800 in casing 6700 of insertion instrument 6600 (compare FIGS. 37 and 41) and subsequently insertion instrument 6600 can be completely removed from the operation area (compare FIG. 42). FIG. 43 illustrates in which manner a bone screw 20 traversely passes through the intervertebral space and intervertebral disk prosthesis 6000 in particular in the area of first recesses 6100c, 6200c of shanks 6100, 6200, whereas in FIGS. 38 to 43 bone screw 20 is shown only in section. A lateral view of the incorporated situation of intervertebral disk prosthesis 6000 into the intervertebral space between the two adjacent vertebral bodies 100, 200 is shown in FIG. 44. In particular, the connection line 70, along which bone screw 20 connects the two vertebral bodies 100, 200, is shown.

Figure 46:
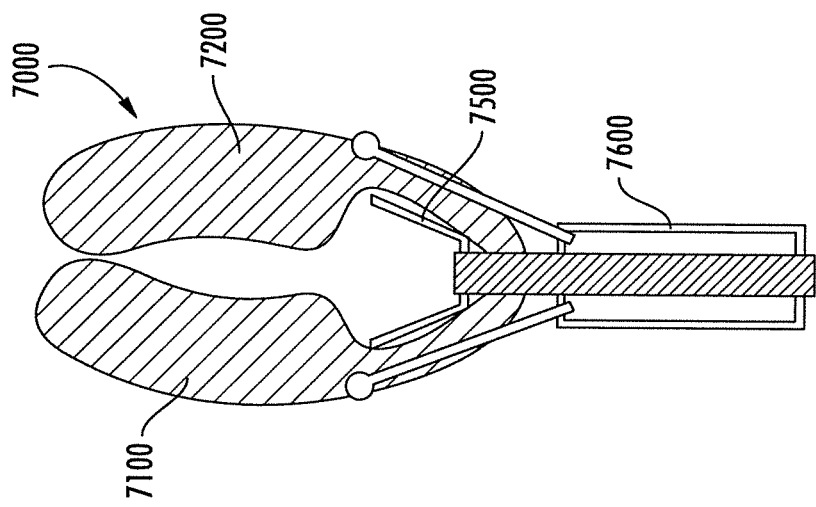
FIG. 46 shows the intervertebral disk prosthesis according to FIG. 45 with holder.
Figure 45:
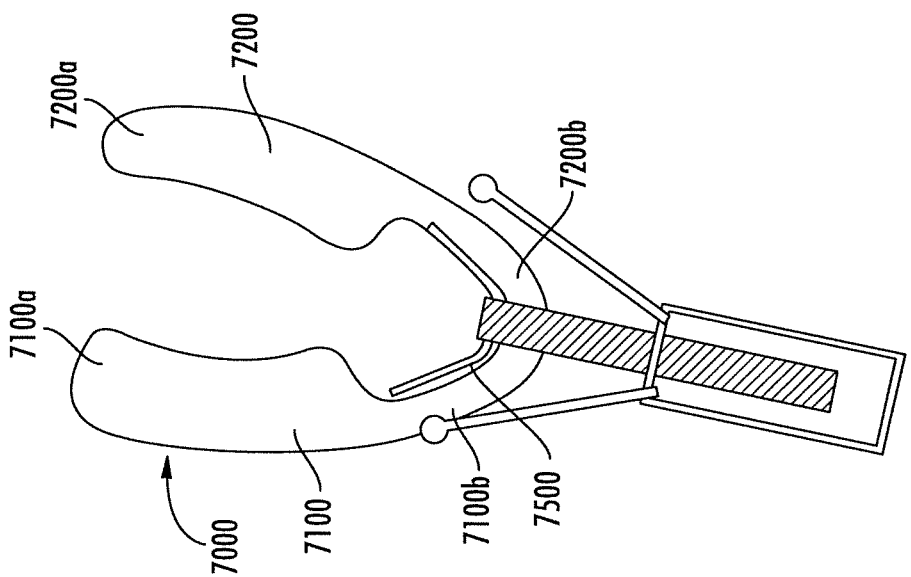
FIG. 45 shows a seventh exemplary embodiment of an intervertebral disk prosthesis with holder.

FIGS. 45 to 48 show a seventh exemplary embodiment of an intervertebral disk prosthesis 7000 that has a first shank 7100 with a first end 7100a and a second end 7100b as well as has a second shank 7200 with a first end 7200a and a second end 7200b. The two shanks 7100, 7200 can be connected to one another to one piece or can be constructed as a separate shank. Instead of spring element 6500, according to the sixth exemplary embodiment a spring element 7500 consisting of a memory alloy is arranged between the two shanks 7100, 7200. The memory alloy is designed in particular in such a manner that the form is changed upon reaching the body temperature. FIG. 45 shows an intervertebral disk prosthesis 7000 with the two shanks 7100, k7200 in the closed position, in which intervertebral disk prosthesis 7000 can be introduced into the intervertebral space. This takes place in particular at a temperature that is slightly below the body temperature, in particular at room temperature, so that spring element 7500 rests on the two shanks 7100, 7200 and, if necessary, additionally supports the holding of shanks 7100, 7200 in the closed position. FIG. 46 shows the widening open of spring element 75 upon reaching the body temperature based on the memory effect, whereby spring element 7500 spreads open in such a manner that shanks 7100, 7200 are pivoted against one another.

Figure 48:
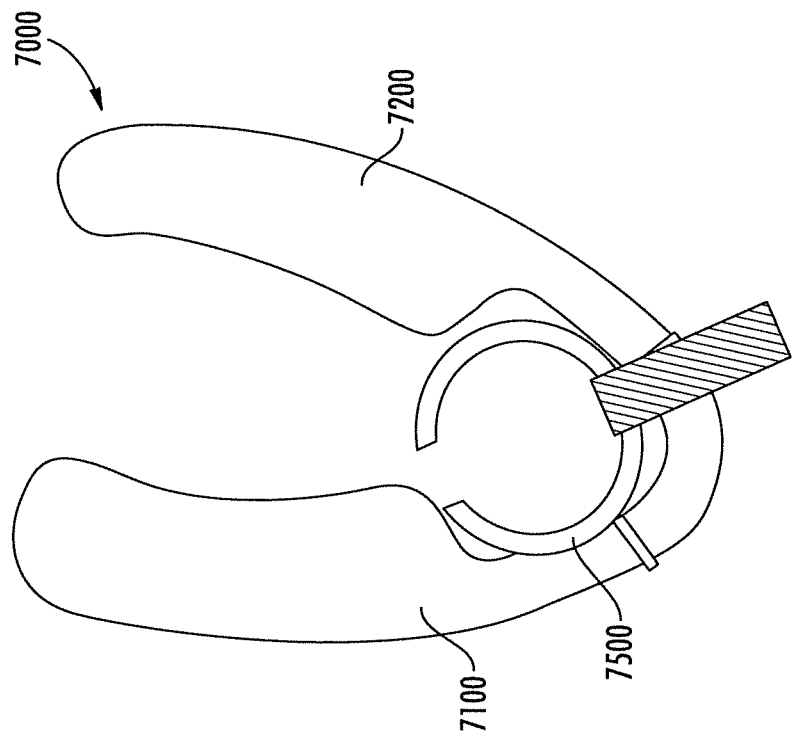
FIG. 48 shows the intervertebral disk prosthesis according to FIG. 47 in another position.
Figure 47:
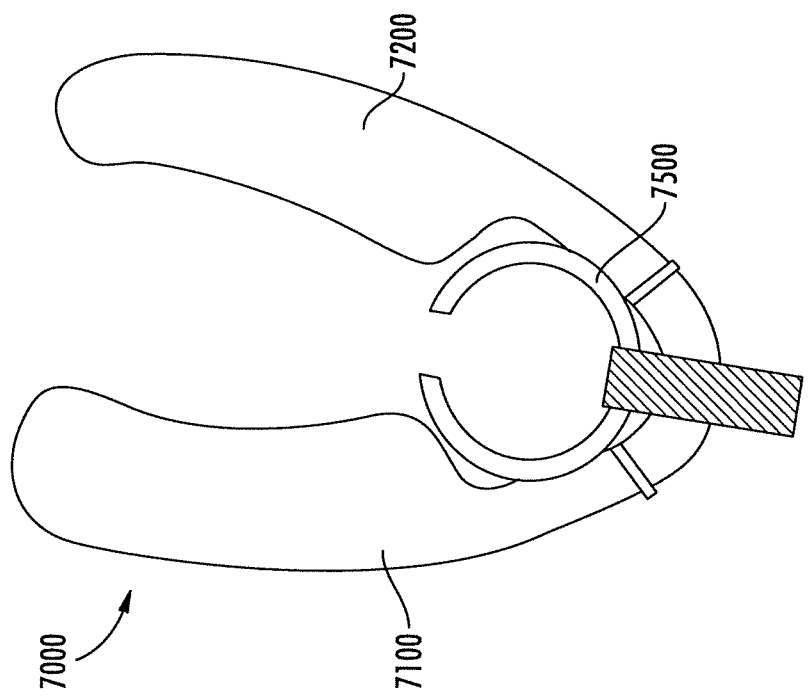
FIG. 47 shows the intervertebral disk prosthesis according to FIG. 45 with an alternative spring element.

Intervertebral disk 7000 can subsequently be moved into the desired position in the intervertebral space with an insertion instrument 7600 comparable to insertion instrument 6600 in accordance with the sixth exemplary embodiment in order to subsequently remove insertion instrument 7600, whereby intervertebral disk prosthesis 7000 remains in the spread-open position by spring element 7500. Spring element 7500 in accordance with FIGS. 45 and 46 has two elements in the manner of leaf-spring shanks. Alternatively, as shown in FIGS. 47 and 48, spring element 7500 can also be constructed as a slotted easing with two curved shanks.

The features from the different exemplary embodiments can also be combined in any desired manner.

Shanks 1100, 1200, 2100, 2200, 3100, 3200, 4100, 4200, 5100, 5200, 6100, 6200, 7100, 7200 of intervertebral disk prostheses 1000, 2000, 3000, 4000, 5000, 6000, 7000 can all be manufactured from an elastic material. However, shanks 1100, 1200, 2100, 2200, 3100, 3200, 4100, 4200, 5100, 5200, 6100, 6200, 7100, 7200, are preferably manufactured from PEEK (polyetheretherketone),

What is claimed is:

1. A process, for introducing an intervertebral disk prosthesis into an intervertebral space defined between two adjacent vertebral bodies of a vertebral column having a plurality of adjacent vertebral bodies arrayed along a common longitudinal direction plane of said vertebral column, comprising the steps of:
   providing an intervertebral disk prosthesis;
   identifying a single extraforaminal access point proximate said intervertebral space, wherein the single extraforaminal access point is located dorsally such that an access from the single extraforaminal access point to the intervertebral space is not guided through a foramen;
   introducing said intervertebral disk prosthesis laterally through said single extraforaminal access point into said intervertebral space between a superior vertebral body and an inferior vertebral body of said adjacent vertebral bodies of said vertebral column,
   wherein said step of introducing said intervertebral disk prosthesis is performed in a linear orientation along a line that is acute to said common longitudinal direction plane of said vertebral column without intersecting a pedicle or any space between pedicles of said adjacent vertebral bodies, and
   wherein said step of introducing said intervertebral disk prosthesis does not damage the foramen.

2. The process, according to claim 1, whereby:
   prior to said step of introducing said intervertebral disk prosthesis, said process further comprising the steps of:
   accessing an external set of nerve roots proximate said single extraforaminal access point and said intervertebral space; and
   pressing said set of nerve roots in either an inferior-medially direction or a superior-laterally direction.

3. The process, according to claim 1, further comprising the steps of:
   providing a first fixation screw;
   introducing said first fixation screw through said extraforaminal access point in either a transpedicularly direction or an extrapedicularly direction;
   said step of introducing said first fixation screw being in a linear orientation along a line that is acute to said common longitudinal direction plane of said vertebral column;
   and
   attaching said first fixation screw to one of said two adjacent vertebral bodies.

4. The process, according to claim 3, further comprising the steps of:
   providing a second fixation screw;
   introducing said second fixation screw through said extraforaminal access point in either a transpedicularly direction or a extrapedicularly direction; and
   attaching said second fixation screw to a second of said two adjacent vertebral bodies.

5. The process, according to claim 4, further comprising the steps of:
   fastening a rod between said first fixation screw and said second fixation screw.

6. The process according to claim 1, wherein an intervertebral disk prosthesis is used, which has a substantially U-shape and has a first shank and a second shank.

7. The process according to claim 1, wherein said single extraforaminal access point is located more than 4.5 cm laterally away from the sagittal plane.

8. The process according to claim 7, wherein said the single extraforaminal access leads transversally to the two adjacent vertebral bodies.

* * * * *